(12) United States Patent
Mathur et al.

(10) Patent No.: US 10,368,782 B2
(45) Date of Patent: Aug. 6, 2019

(54) ELECTRO-MEDICAL SYSTEM FOR NEURO-MUSCULAR PARALYSIS ASSESSMENT

(71) Applicant: Ondine Tech Inc., Morgan Hill, CA (US)

(72) Inventors: Amitabh Mohan Mathur, Morgan Hill, CA (US); Radhey Mohan Mathur, Morgan Hill, CA (US); Arun Kumar Sharma, Cupertino, CA (US); Venkata Murthy Durvasula, El Dorado Hills, CA (US)

(73) Assignee: Ondine Tech Inc., Morgan Hill, CA (US)

( * ) Notice: Subject to any disclaimer, the term of this patent is extended or adjusted under 35 U.S.C. 154(b) by 953 days.

(21) Appl. No.: 13/844,560

(22) Filed: Mar. 15, 2013

(65) Prior Publication Data

US 2013/0331711 A1 Dec. 12, 2013

Related U.S. Application Data

(60) Provisional application No. 61/657,779, filed on Jun. 9, 2012.

(51) Int. Cl.
*A61B 5/11* (2006.01)
*A61B 5/0205* (2006.01)

(52) U.S. Cl.
CPC .......... *A61B 5/1106* (2013.01); *A61B 5/0205* (2013.01); *A61B 2505/05* (2013.01); *A61B 2562/0219* (2013.01)

(58) Field of Classification Search
CPC . A61B 5/1106; A61B 5/0205; A61B 2505/05; A61B 2562/0219
See application file for complete search history.

(56) References Cited

U.S. PATENT DOCUMENTS

| | | | |
|---|---|---|---|
| 2,808,826 A | * 10/1957 | Reiner | A61B 5/05 323/911 |
| 4,291,705 A | * 9/1981 | Severinghaus | A61B 5/0488 600/546 |

(Continued)

FOREIGN PATENT DOCUMENTS

| GB | 2113846 A | 8/1983 |
|---|---|---|
| KR | 10-2012-000370 A | 2/2012 |

OTHER PUBLICATIONS

Burke et al. ("The effects of a volatile anaesthetic on the excitability of human corticospinal axons," Grain (2000), vol. 123, p. 992-1000).*

(Continued)

*Primary Examiner* — Rene T Towa
(74) *Attorney, Agent, or Firm* — Innovation Counsel LLP

(57) ABSTRACT

A computer-implemented method for quantitatively determining a person's neuro-muscular blockade (NMB) level in real-time using at least one sensor attached to the person is provided. The method includes receiving a first input signal from the sensor, wherein the first input signal includes a measurement of a first muscular response, the first muscular response resulting from a baseline stimulus current delivered to the person before administration of NMB agents to the person, and establishing a baseline chronaxie based on the first input signal. The method also includes delivering one or more stimulus currents to the person after the administration of NMB agents to the person, receiving a second input signal from the sensor, wherein the second input signal includes a measurement of one or more muscular responses resulting from the one or more stimulus currents, and determining the person's NMB level based on the second input signal.

17 Claims, 32 Drawing Sheets

(56) References Cited

U.S. PATENT DOCUMENTS

| | | | | |
|---|---|---|---|---|
| 4,387,723 A * | 6/1983 | Atlee, III | ............. | A61B 5/1106 600/547 |
| 5,131,401 A | 7/1992 | Westenskow | | |
| 5,891,050 A | 4/1999 | Gansler et al. | | |
| 6,016,444 A | 1/2000 | John | | |
| 6,573,103 B1 * | 6/2003 | Wald | ................... | G01N 33/689 435/4 |
| 6,615,082 B1 * | 9/2003 | Mandell | ............... | A61N 1/3712 607/11 |
| 2004/0068229 A1 * | 4/2004 | Jansen | ................ | A61M 5/1723 604/154 |
| 2004/0243017 A1 | 12/2004 | Causevic | | |
| 2007/0015972 A1 | 1/2007 | Wang et al. | | |
| 2009/0327204 A1 * | 12/2009 | Gilhuly | ................. | G05B 17/02 706/54 |
| 2010/0081963 A1 * | 4/2010 | Gilhuly | ................. | G05B 17/02 600/554 |
| 2013/0204156 A1 * | 8/2013 | Hampton | ............. | A61B 5/1106 600/546 |

OTHER PUBLICATIONS

KIPO International Search Report corresponding to PCT/US2013/040400, dated Aug. 27, 2013, 2 pages.
B.C. Tsui "The Effects of General Anasthesia on Nerve-Motor Response Characteristics (rheobase and chronaxie) to Peripheral Nerve Stimulation" Anastethesia, vol. 69, No. 4, pp. 374-379; Apr. 18, 2014.
Geddes L A, "Accuracy Limitations of Chronaxie Values", IEEE Transactions on Biomedical Engineering, IEEE Service Center, vol. 51, No. 1, pp. 176-181, Jan. 1, 2004.
European Search Report EP13801214 dated Jan. 5, 2016.

\* cited by examiner

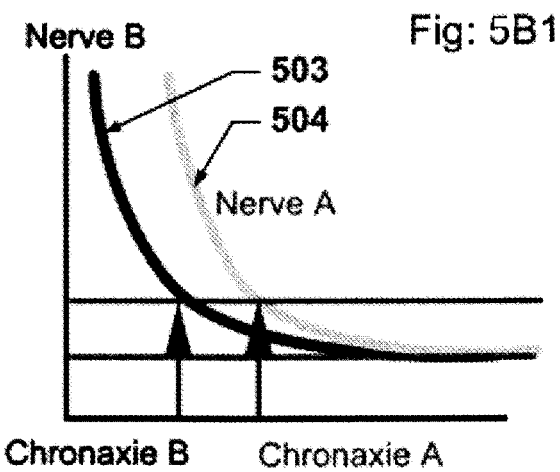
Fig: 5B1
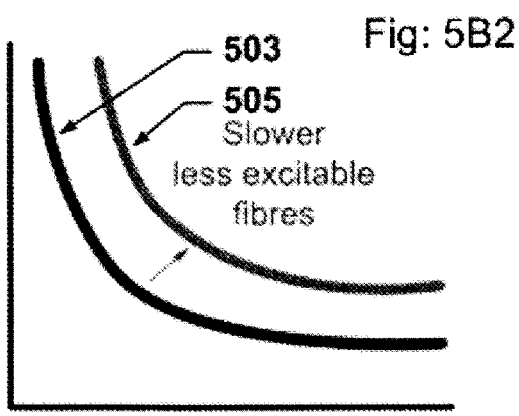
Fig: 5B2
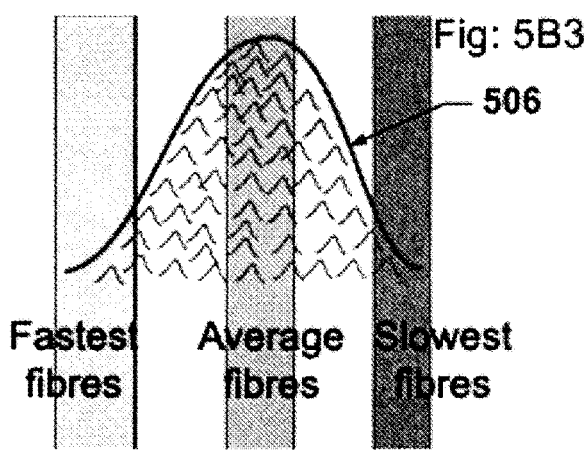
Fig: 5B3

ELECTRO-MEDICAL SYSTEM FOR NEURO-MUSCULAR PARALYSIS ASSESSMENT

CROSS REFERENCE TO RELATED APPLICATIONS

The present application claims the benefit of U.S. Provisional Patent Application No. 61/657,779 entitled "ELECTRO-MEDICAL SYSTEM FOR NEURO-MUSCULAR PARALYSIS ASSESSMENT," which was filed on Jun. 9, 2012.

FIELD OF INVENTION

The present invention relates to an improved electro-medical device system, suitable for determining the extent of neuro-muscular blockade (NMB) during hospital operation room administration of general anesthesia, other medical procedures and medical attention to in face of neurotoxin based chemical accidents. The device uses the physiological concept of Chronaxie to determine the patient's level of neuro-muscular blockade in digital and quantitative format under an anesthesia agent. The device is suitable to operate in an electrical energy budget constraint, and more particularly, to a very low-powered, wirelesses or wired, non-invasive patient monitoring system.

In the existing state of the art (e.g., current twitch monitors), the assessment is subjective. This invention adds sensory instrumentation and quantification method to remove the subjective assessment.

BACKGROUND OF THE INVENTION

In an operating room, for any surgery requiring general anesthesia, the patient is given an intravenous or intramuscular dose of potent paralytic drugs (Neuro-muscular blocking agents (NMBA) (e.g. Vecuronium). These drugs are given after the induction of anesthesia (before surgery begins), and re-dosed during long duration surgeries, to ensure that a state of paralysis is maintained throughout the entire surgical course. At the end of surgery, the anesthesia provider has to make a judgment regarding the degree of paralysis of the patient so that a correct dose of antidote, or NMB Reversing Agent (NMBRA) (e.g. Neostigmine), can be administered to reverse the paralysis. Upon receiving the correct dose of NMBRA, the patient regains consciousness and is brought back to a state of wakefulness.

The success of administering and reversing general anesthesia depends heavily on using the correct dose of NMBA and NMBRA. More specifically, an excessive dose as well as a low dose of antidote can be dangerous and life threatening. Administering excessive NMB antidote runs the risk of recurarization in some patients. Recurarization is subjective to a patient and his condition; it is not predictable, nor easily reproducible. Failure to recognize and promptly treat recurarization often leads to death.

Currently, there are some electro-medical devices under various names such as Peripheral Nerve Stimulator (U.S. Pat. Nos. 4,157,087, 5,131,401) etc., that provide a modicum of monitoring of patients under anesthesia using NMBA. However, clinical criteria are subjective, causing doubt about clinical residual NMB.

A problem with current patient monitoring systems is the lack of a quantitative measure of the degree of patient neuro-muscular blockade (paralysis). Most anesthesiologists today use a method of directing a train of electrical pulses toward a patient nerve in select area (e.g., the thumb) and observing patient response (e.g., twitching of the thumb). The patient response varies from individual to individual significantly. Yet, there is no device that helps the anesthesiologist accurately determine the end point of the paralysis. Determining the dose of NMBRA to use remains an "art" based on the anesthesia provider's memory, experience, and judgment.

The current devices emit four electrical pulses (also known in the industry as "Train Of Four" (TOF)) that are directed towards a nerve on the surface of the skin, which further supply electrical impulses to a muscle group. A patient's muscle has a unique neuromuscular threshold to electrical stimulation that is further modulated by electrode placement and quality of electrode's electrical contact with the skin, and currently available devices are unable to factor in these neuromuscular thresholds. Some devices do not keep a record of the electrical pulses administered and/or the corresponding patient's response to the stimulus to an electrical 'train of four'. The practice depends on the anesthesiologist's training and experience. Therefore, there is little to no quantitative measure of the extent of neuro-muscular blockade and the gradual wearing out of the efficacy of the paralytic drugs administered with the current generation of diagnostic devices that are commercially available.

The current diagnostic devices that try to instrument and measure the twitch due to TOF are subjective and based on the assessment of the anesthesia doctor. Furthermore, they do not provide robust quantification of degree of paralysis to aid determination of the dosage of NMB-reversal agent (NMBRA) that should be administered to quickly and safely bring back the patient to recovery, a natural phase of breathing, and wakefulness. This quite often is one of the causes of death after anesthesia and surgery. The Journal of Anesthesia and Analgesia, July 2010 commented upon this lamentable state of affairs in a series of articles among other medical literature in anesthesia.

At least based on the above, there is a need for a device that can accurately measure NMB and give reliable information to determine patient's level of paralysis, guiding the anesthesiologist's determination of correct NMBRA dosage. Such a device would aid patient recovery during and after the end of clinical anesthesia in the operating room, and reduce the chances of partial reversal due to inaccurate assessment and consequent over-dosing, which often results in deaths at post operative care unit or intensive care unit.

SUMMARY

In one aspect, the inventive concept pertains to a computer-implemented method for quantitatively determining a person's neuro-muscular blockade (NMB) level in real-time using at least one sensor attached to the person. The method includes receiving a first input signal from the sensor, wherein the first input signal includes a measurement of a first muscular response, the first muscular response resulting from a baseline stimulus current delivered to the person before administration of NMB agents to the person, and establishing a baseline chronaxie based on the first input signal. The method also includes delivering one or more stimulus currents to the person after the administration of NMB agents to the person, receiving a second input signal from the sensor, wherein the second input signal includes a measurement of one or more muscular responses resulting from the one or more stimulus currents, and determining the person's NMB level based on the second input signal.

In another aspect, the inventive concept pertains to an apparatus for quantitatively determining a person's neuromuscular blockade (NMB) level in real-time using at least one sensor attached to the person. The apparatus includes a sensing system comprising the sensor and at least one stimulus electrode, the stimulus electrode for delivering a stimulus current to the person and the sensor for measuring a muscular response of the person, the sensing system configured to transmit a signal including a measurement of the muscular response, and a paralysis assessment system configured to receive the signal and determine the person's NMB level based on the signal.

In yet another aspect, the inventive concept pertains to a non-transitory computer-readable medium storing instructions that, when executed, causes a computer to perform a method for quantitatively determining a person's neuromuscular blockade (NMB) level in real-time using at least one sensor attached to the person. The method includes receiving a first input signal from the sensor, wherein the first input signal includes a measurement of a first muscular response, the first muscular response resulting from a baseline stimulus current delivered to the person before administration of NMB agents to the person, and establishing a baseline chronaxie based on the first input signal. The method also includes delivering one or more stimulus currents to the person after the administration of NMB agents to the person, receiving a second input signal from the sensor, wherein the second input signal includes a measurement of one or more muscular responses resulting from the one or more stimulus currents, and determining the person's NMB level based on the second input signal.

BRIEF DESCRIPTION OF DRAWINGS

FIGS. 5B1 to 5B3 illustrate how different muscles can behave differently even under the same stimuli conditions.

FIGS. 20, 21, 22, 23, 24, 25, 26, 27, 28, and 29 are flow charts illustrating exemplary methods and sub-processes according to different embodiments of the invention.

FIG. 20 is a main workflow that starts with "Power Switch ON" 350.

FIG. 22 is a flow chart for the sub-process "Measure Chronaxie" 405.

FIG. 23 is a flow chart for the sub-process "Measure relative chronaxie" 406.

FIG. 24 is a flow chart for the sub-process "Compute and display NMB Parameter and Mathur Parameter" 407.

FIG. 25 is a flow chart for the sub-process "Measure Rheobase" 416.

FIG. 26 is a flow chart for the sub-process "Measure background noise, twitch baseline and range" 399.

FIG. 27 is a flow chart for the sub-process "Measure background noise" 473.

FIG. 28 is a flow chart for the sub-process "Pre-stimulus setup" 436.

FIG. 29 is a flow chart for the sub-process "Post-stimulus setup" 490.

DETAILED DESCRIPTION

The following description is of the best mode presently contemplated for carrying out the invention. It is not to be taken in limiting sense, but is made merely for the purpose of describing the general principles of the invention.

Reference will now be made in detail to the exemplary embodiments illustrated in the accompanying drawings. Wherever possible, the same reference numbers will be used throughout the drawings to refer to the same or like parts.

Figure 1:
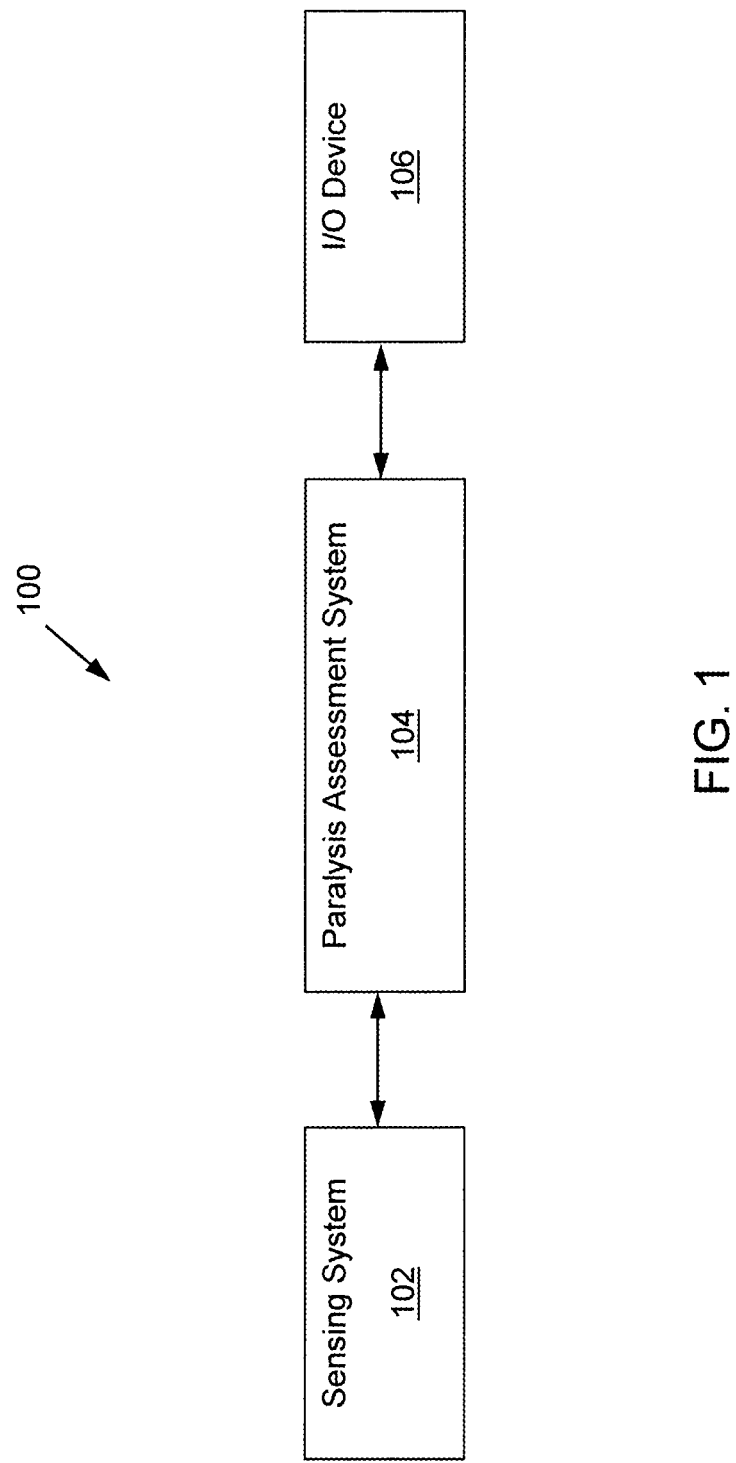
FIG. 1 illustrates a block diagram of an exemplary system 100 consistent with the invention.

FIG. 1 illustrates a block diagram of an exemplary system 100 consistent with the invention. As shown in FIG. 1, exemplary system 100 may include a sensing system 102, a paralysis assessment system 104, and an input/output (I/O) device 106. Each of the components is operatively connected to one another via a network or any type of communication links that allow transmission of data from one component to another. The network may include Local Area Networks (LANs) and/or Wide Area Networks (WANs), and may be wireless, wired, or a combination thereof.

The sensing system 102 can include sensors and/or actuating sources. The sensors can include twitch sensor(s) that are suitably mounted on body part, to measure physical movement due to twitching of target muscle.

The sensors can also include auxiliary motion sensor(s). The auxiliary motion sensor is similar to a twitch sensor, but is mounted on a body part separate from the target body part where the twitch sensor is mounted, and where the body part remains unaffected by stimulus (e.g., an electrical stimulus).

The sensors can further include eyelid sensor(s). For example, eye-brow twitch sensors (such as the Tilak Unit, which is produced by Ondine Tech) may be used. The eyelid sensor is mounted near the eye, on the forehead, or a nearby area (for example below the eye-brow).

In some embodiments, more than one type of sensor may be used at the same time to improve accuracy (i.e., higher signal-to-noise ratio), confidence level of data, and system robustness.

The transducer element(s) in the sensors can be of different types, and can include transducers that measure motion, force, or stress along one or more axis. For example, the sensor transducer element can include, and is not limited to, rate gyro sensors (measuring angular acceleration), linear accelerometers, vibration sensors, piezo sensors (electric or resistive), magnetic coil sensors, inductive sensors, or strain gauges.

Sensor performance is important when selecting an appropriate sensor for the sensing system 102. For example, a sensor may be selected based on criteria such as average power consumption, detection sensitivity, Type-1 error probability, Type-2 error probability, repeatability, etc.

Figure 2A:
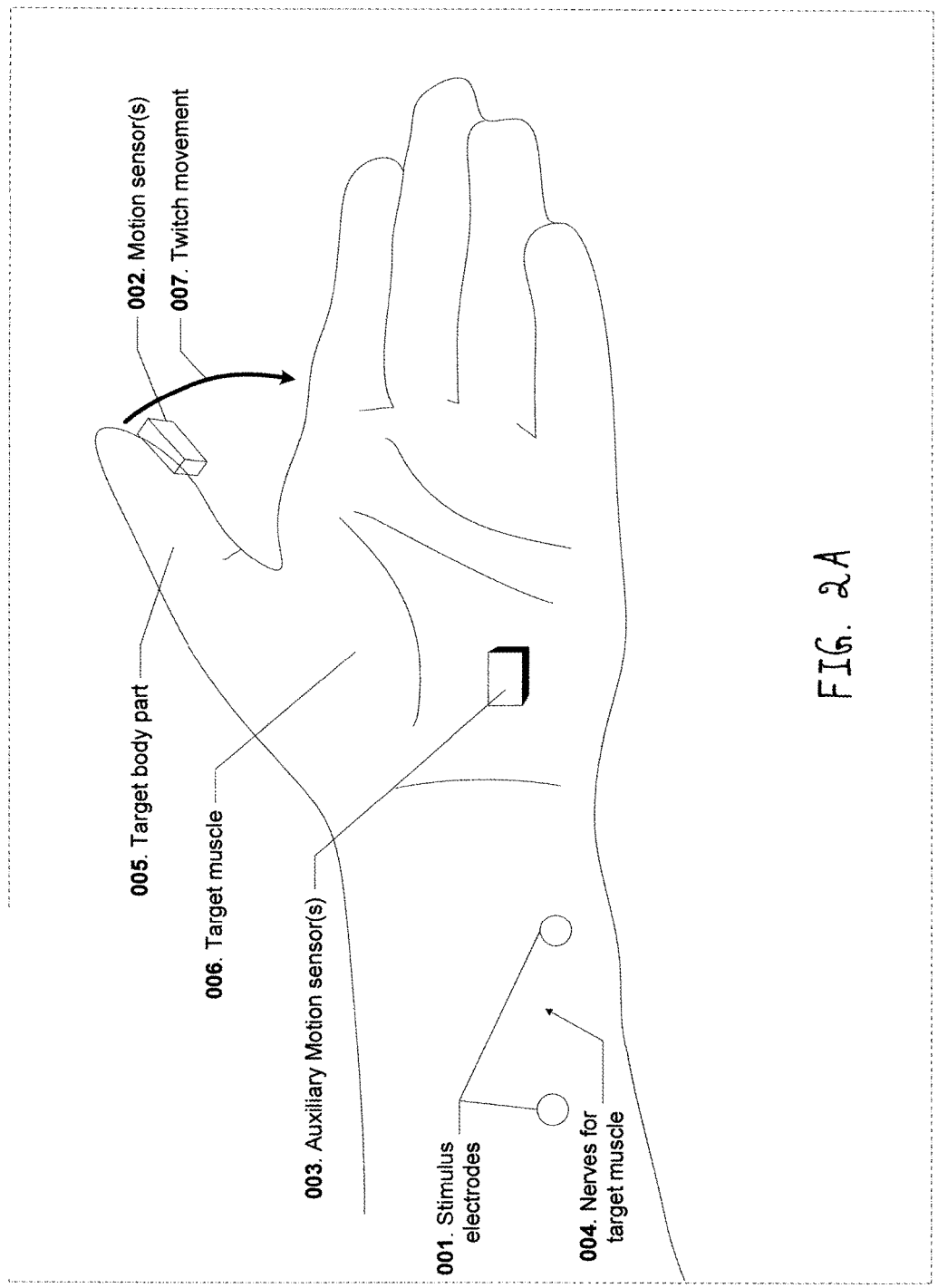
FIG. 2A shows an embodiment of the sensing system 102 of FIG. 1.
Figure 2B:
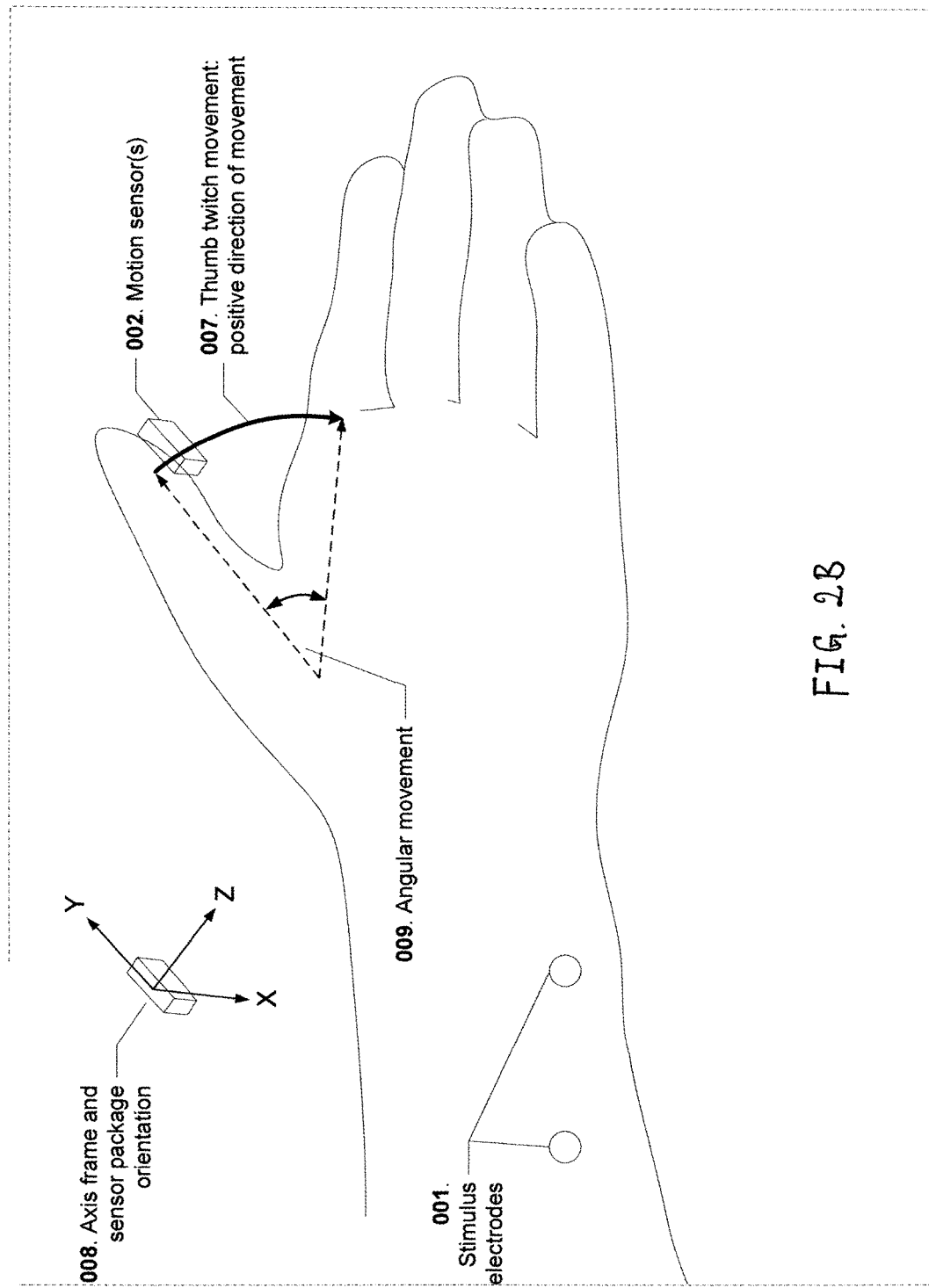
FIG. 2B shows the physiological movement and sensor frame of the sensing system 102 in FIG. 2A.

As mentioned above, the sensing system 102 also includes actuating sources. The actuating sources can be provided in the form of stimulus electrodes 001 (as shown in FIGS. 2A and 2B). The stimulus electrodes 001 send an electrical pulse to the nerves corresponding to the target muscle, which causes the muscle to twitch. The physical movement due to the twitching of the target muscle is then measured using the sensor mounted on a body part.

As shown in FIG. 1, paralysis assessment system 104 can be implemented as a software program executing in a processor and/or as hardware that performs a paralysis analysis based on the measured NMB. The NMB is measured by the signals provided from the sensing system 102. The paralysis assessment system 104 can, for example, determine the NMB parameter of a patient. The determination of the NMB parameter using the paralysis assessment system 104 will be described in detail later in the specification.

With reference to FIG. 1, the I/O device 106 can be, for example, a computer, personal digital assistant (PDA), cell phone or smartphone, laptop, desktop, a tablet PC, media content player, set-top box, television set including a broadcast tuner, or any electronic device capable of accessing a data network and/or receiving imaging data. In some embodiments, the I/O device 106 can be a display device such as, for example, a television, monitor, projector, display panel, or any other display device. In certain embodiments, the I/O device 106 can be a printer.

While shown in FIG. 1 as separate components that are operatively connected, any or all of sensing system 102, paralysis assessment system 104, and I/O device 106 may be co-located in one device. For example, sensing system 102 can be located within or form part of paralysis assessment system 104 or I/O device 106, paralysis assessment system 104 can be located within or form part of sensing system 102 or I/O device 106, or I/O device 106 can be located within or form part of sensing system 102 or paralysis assessment system 104. It is understood that the configuration shown in FIG. 1 is for illustrative purposes only. Certain components or devices may be removed or combined and other components or devices may be added.

To aid in understanding the invention, a brief description of nerve and muscle behavior is herein provided.

During surgery in operating rooms, patients are given Neuro-Muscular Blockade (NMB) drugs to block the movement of muscles during surgery. NMB drugs induce a paralyzed state for the patient where no movement is possible any longer. This also means that the patient is unable to breathe on their own, and all breathing needs to be assisted manually or a ventilator.

When a patient is in a paralyzed state, the patient's body may be under different states of relaxation. The state of relaxation is determined by the degree of flaccidity obtained in a muscle by blocking the Neuro-Muscular Receptor at the neuromuscular junction using injectable NMB drugs.

Although the muscles may be flaccid when the patient is in a paralyzed state, the muscles can still exhibit a physiological response to nervous system stimulus (which is electrical in nature). The physiological response is a function of the intensity (e.g., current) of the electrical stimulus and its duration (i.e., the length of time that the electrical stimulus is being applied to the nerve of the muscle group).

The physiological response can be characterized by parameters such as rheobase and chronaxie. The rheobase is a measure of the minimum electrical current required to stimulate a Neuro-Muscular group in the body. The chronaxie is a measure of the minimum time required to stimulate a neuro-muscular group (muscle fiber or nerve cell), using an excitation current that is twice the rheobase (i.e., double the strength of the rheobase).

Figure 3:
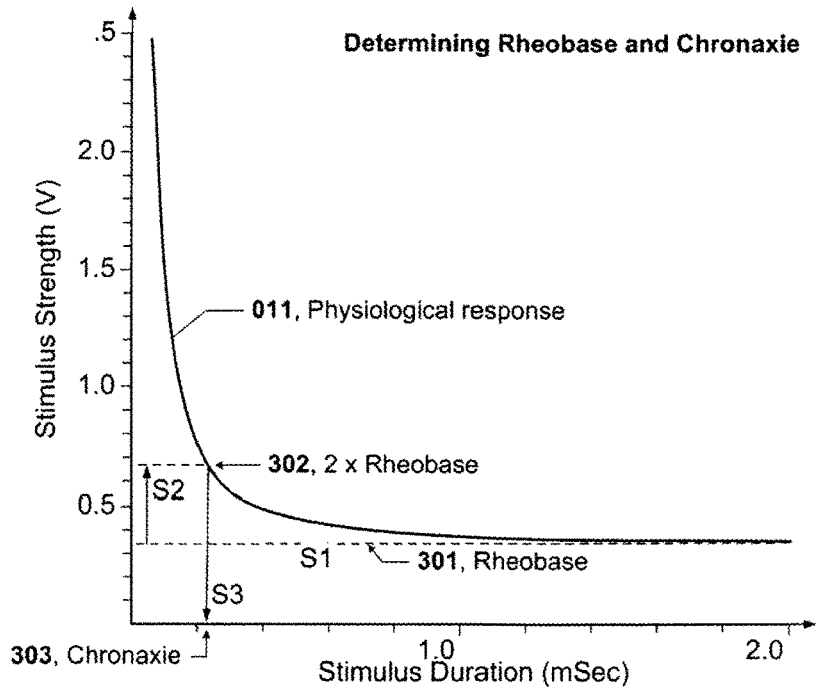
FIG. 3 illustrates how the chronaxie and rheobase can be determined when a stimulus is applied directly to the nerves.

FIG. 3 illustrates how the chronaxie and rheobase can be determined when a stimulus is applied directly to the nerves. In FIG. 3, the Strength-Duration curve 011 measures the physiological response as a function of stimulus strength (V) and stimulus duration (mSec). The rheobase 301 is the minimum Stimulus Strength that will produce a physiological response. The chronaxie 303 is the Stimulus Duration that yields a response when the Stimulus Strength is set to exactly twice the rheobase.

Referring to FIG. 3, the rheobase 301 is determined by the voltage at which the Strength-Duration curve 011 asymptotes. As shown in FIG. 3, the rheobase 301 has a value of about 0.35 V. To determine the chronaxie 303, an excitation current 302 corresponding to twice the rheobase 301 is first calculated. As shown in FIG. 3, the excitation current 302 is about 0.7 V (given 2×~0.35 V). Next, the chronaxie 303 is determined by extrapolating a line down to the Stimulation Duration axis. As shown in FIG. 3, the chronaxie 303 is about 0.22 ms.

Figure 4:
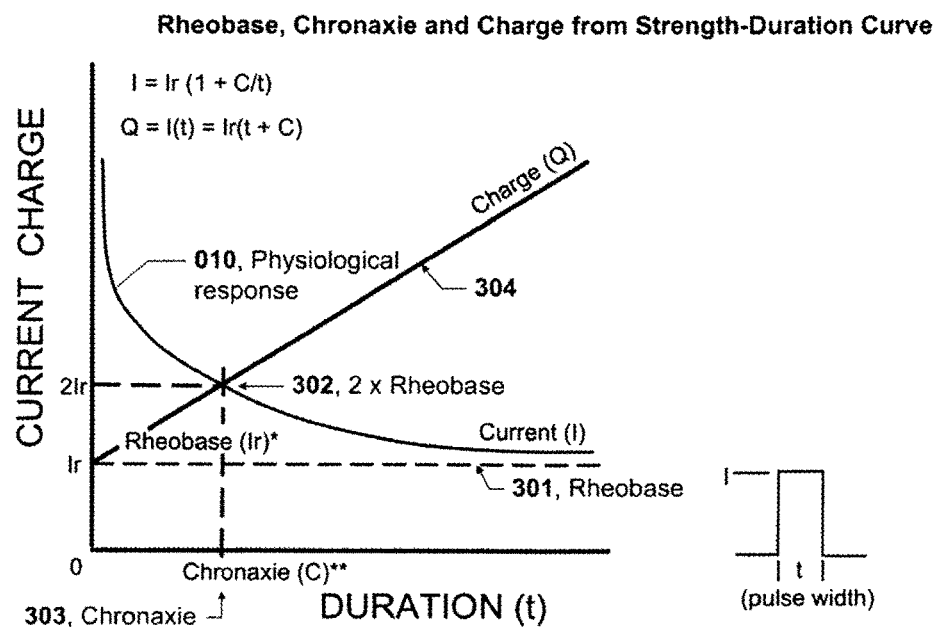
FIG. 4 illustrates an I-D (current-duration) curve.

FIG. 4 illustrates a Stimulus-response curve similar to that shown in FIG. 3. In FIG. 4, the I-D (current-duration) curve 010 is the Stimulus-response. The I-D curve 010 measures the physiological response as a function of current (or charge) and stimulus duration. However, in FIG. 4, the stimulus is not applied directly to the nerve. Instead, the stimulus is applied on skin tissue that is very close to the nerve. The stimulus experienced by the nerve is proportional to the applied current, and hence the Y-axis is given as a measure of the applied current. Furthermore, human skin exhibits non-linear resistance with negative voltage gradient (i.e., the resistance of the skin reduces with higher voltage). Therefore, the applied current is a good measure (indicator) of the actual stimulus experienced by the underlying nerve.

From the curve 011 in FIG. 3 and curve 010 in FIG. 4, it is noted that when the electrical pulse width is reduced (i.e., shorter duration of applied pulse), a greater electrical stimulus is required to elicit a same neuro-muscular response as that prior to the reduction of the electrical pulse width. However, the total electric charge 401 is reduced when the electrical pulse width is reduced, since electric charge is a function of the current over time (Q=I(t)).

Referring to FIG. 4, it can be observed that the I-D curve 010 has an asymptote at the X-axis, which corresponds to the lowest current required to stimulate the nerve when the stimulation pulse duration is infinitely long. The I-D curve 010 is also asymptotic on the Y-axis, whereby the nerve is stimulated by a very short stimulus current period when stimulus current is very high. The curve 010 can be modeled by a mathematical equation, and experimental data can be mapped to calculate the curve's mathematical coefficients using, for example, "Least Squares" method. Generally, an I-D curve is used when the stimulus is not applied directly to the nerve, but to tissues near the nerve.

Pseudo-Chronaxie, NMB Parameter, and Mathur Parameter

Figure 5A:
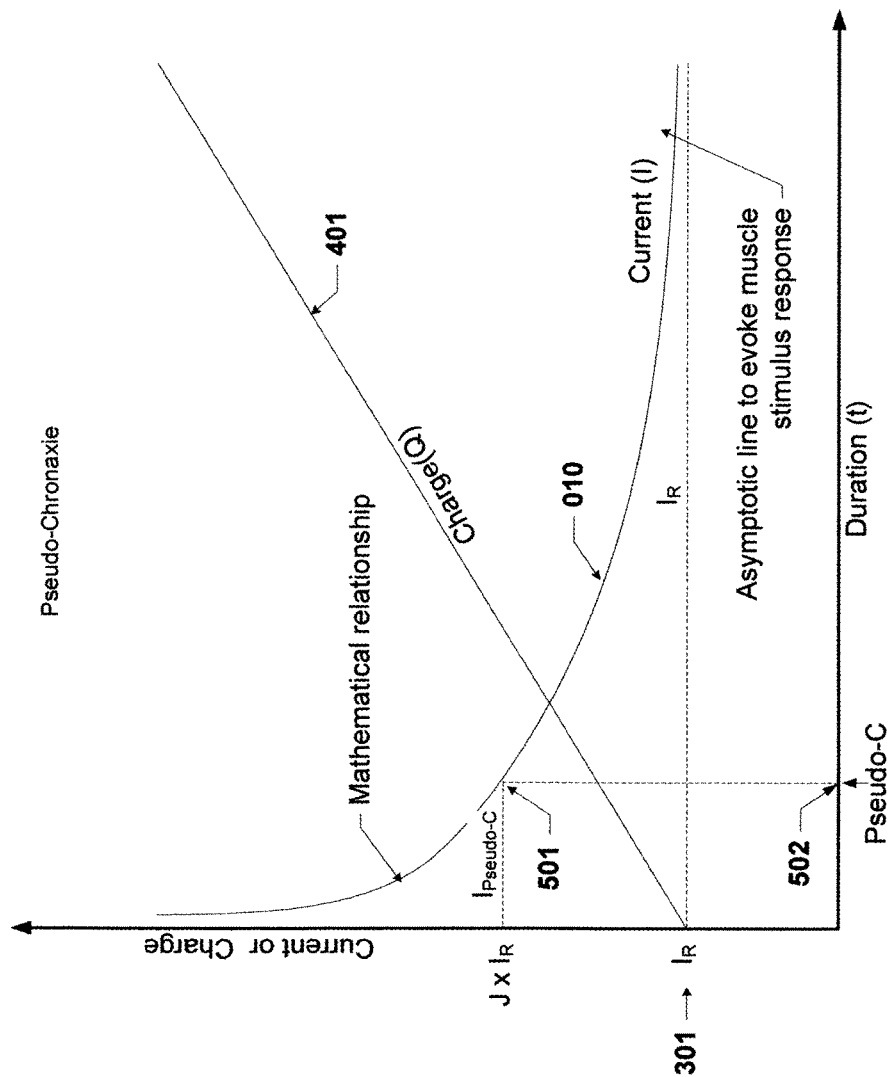
FIG. 5A shows a physiological response curve 010, and how the Pseudo-chronaxie can be obtained from curve 010.

FIG. 5A shows a physiological response curve 010, and how the Pseudo-chronaxie can be obtained from curve 010. The Pseudo-chronaxie is a function of the stimulus current and the duration.

First, the rheobase 301 is determined to be $I_R$. The rheobase 301 corresponds to the minimum stimulus current ($I_R$) that will produce a physiological response.

Next, a 'J' multiplier is selected (where J>1). The stimulus current is then set to $I_{Pseudo-C}$ (given by J multiplied by rheobase). It is noted that the particular case of J=2 corresponds to the "classic" chronaxie. The point 501 on the curve 010 is associated with the scaling multiplier J, and corresponds to the value $I_{Pseudo-C}$.

Next, the Pseudo-Chronaxie 502 is determined by extrapolating from point 501 on the curve 010 to the duration axis. The Pseudo-Chronaxie 502 is the stimulus duration that yields a physiological response when the stimulus current is set to $I_{Pseudo-C}$. As shown in FIG. 5A, the Pseudo-Chronaxie 502 corresponds to a point Pseudo-C on the duration axis.

Stimulating muscle via electrodes attached on skin surface requires moderately high voltage application (typically 30 to 80 Volts). As previously mentioned, the electrical resistance of human skin is non-linear since resistance decreases with increasing voltage (or current). Nevertheless, depending on the choice of stimulus drive electronics, an optimum pseudo-chronaxie multiplier 'k' for conserving operating electrical energy can be determined.

Based on the curve 010 in FIG. 5A, it may be preferable, for efficient energy stimulation, to operate at a portion of the curve that results in the least amount of electric charge and energy used. The current versus time duration response curve for a muscle in an unknown state can be determined by measuring physiological response using several points along the curve, such that less excitation energy is expended. From those points, the Pseudo-chronaxie 502 and classical chronaxie can be determined. Specifically, one can accurately estimate classical chronaxie from the Pseudo-chronaxie 502, and vice versa.

As previously mentioned, the current methods of determining paralysis state via observation can be subjective. The subjectivity and difficulty in ascertaining true paralysis state is further compounded by the fact that different muscles (and muscle groups) can behave differently even under the same stimuli conditions, as described below in with reference to FIGS. 5B1 to 5B3.

Figure 5C:
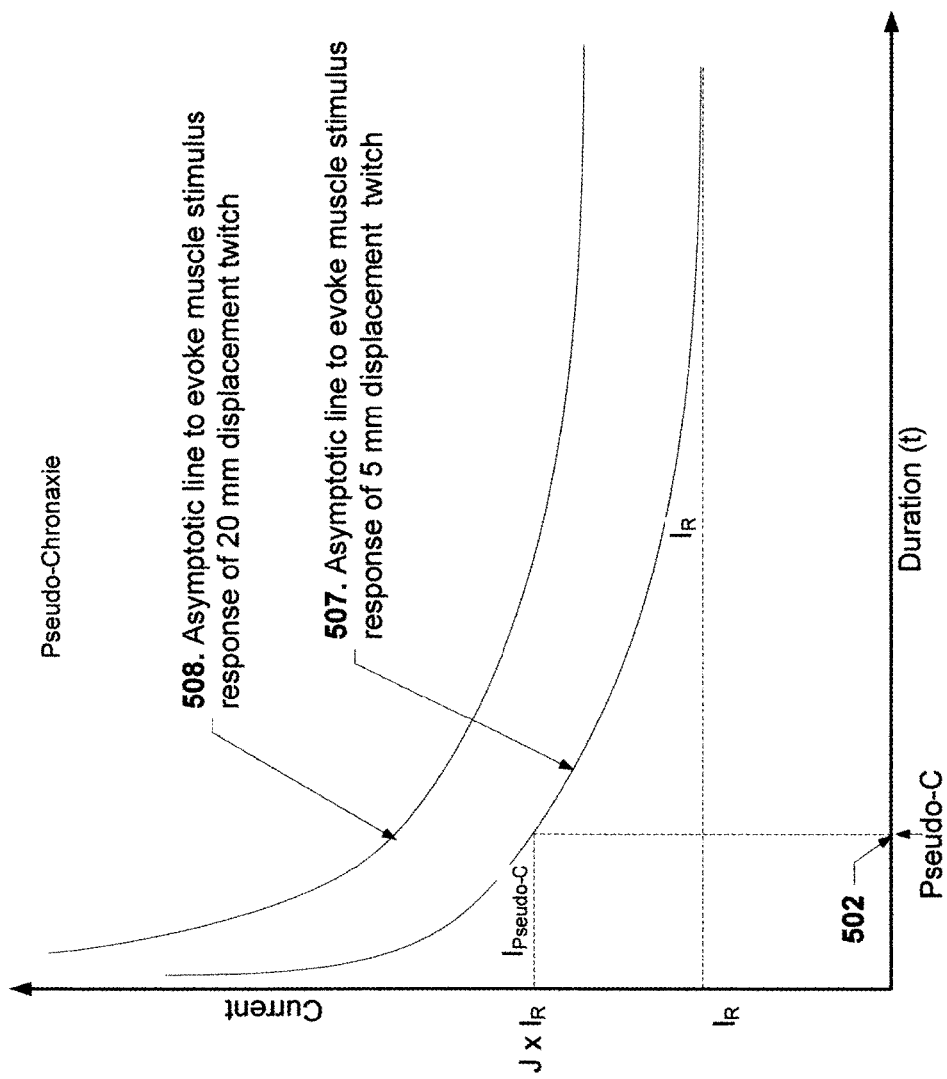
FIG. 5C illustrates the importance of accurately measuring muscle switch intensity to accurately establish Pseudo-chronaxie.

Muscle comprises of numerous fibers and nerve fiber neurons. A typical nerve response is a stochastic activation function as represented by sigmoid function. Due to the constraint of electrode placement on the skin, all axons (in the nerve fibers) are not equally stimulated. In addition, the action potential of axons varies by fiber diameter and statistical dispersion. For example, referring to FIG. 5B3, thicker fibers are more excitable than thinner fiber, and vice versa. Thus, over a large neuro-muscle fiber population sample, the intensity of gross muscle response varies according to excitation current. For example, with reference to FIG. 5C, the curve 507 is associated with a very small physiological response, while the curve 508 is associated with a more robust physiological response.

Referring to FIG. 5B1, nerve-A and nerve-B have the same rheobase. However, from the strength duration curve, it can be observed that nerve-B (503) is more excitable (i.e., having lower chronaxie) than nerve-A (504) (i.e., having a higher chronaxie).

Referring to FIG. 5B2, slow fibers (characterized by curve 505) have higher rheobase and higher chronaxie and are therefore less excitable, compared to quick fibers (characterized by curve 503) that are more excitable.

FIG. 5B3 explains the basis for typical response of nerve bundle, which is the algebraic sum of activation function of individual nerve fiber. The curve 506 is a statistical distribution of activation potential of various nerve fibers in a nerve that ranges from being fast, average, and slow. Thus while a strong stimulus will excite all nerve fibers, a somewhat weaker stimulus will only excite fastest fibers in the nerve bundle, producing a feeble physiological response.

Accordingly, determining an accurate I-D curve of neuromuscle response requires an accurate and repeatable measurement of muscle response. A gross visual recognition by a physician based on the existing methods would not suffice.

Figure 8:
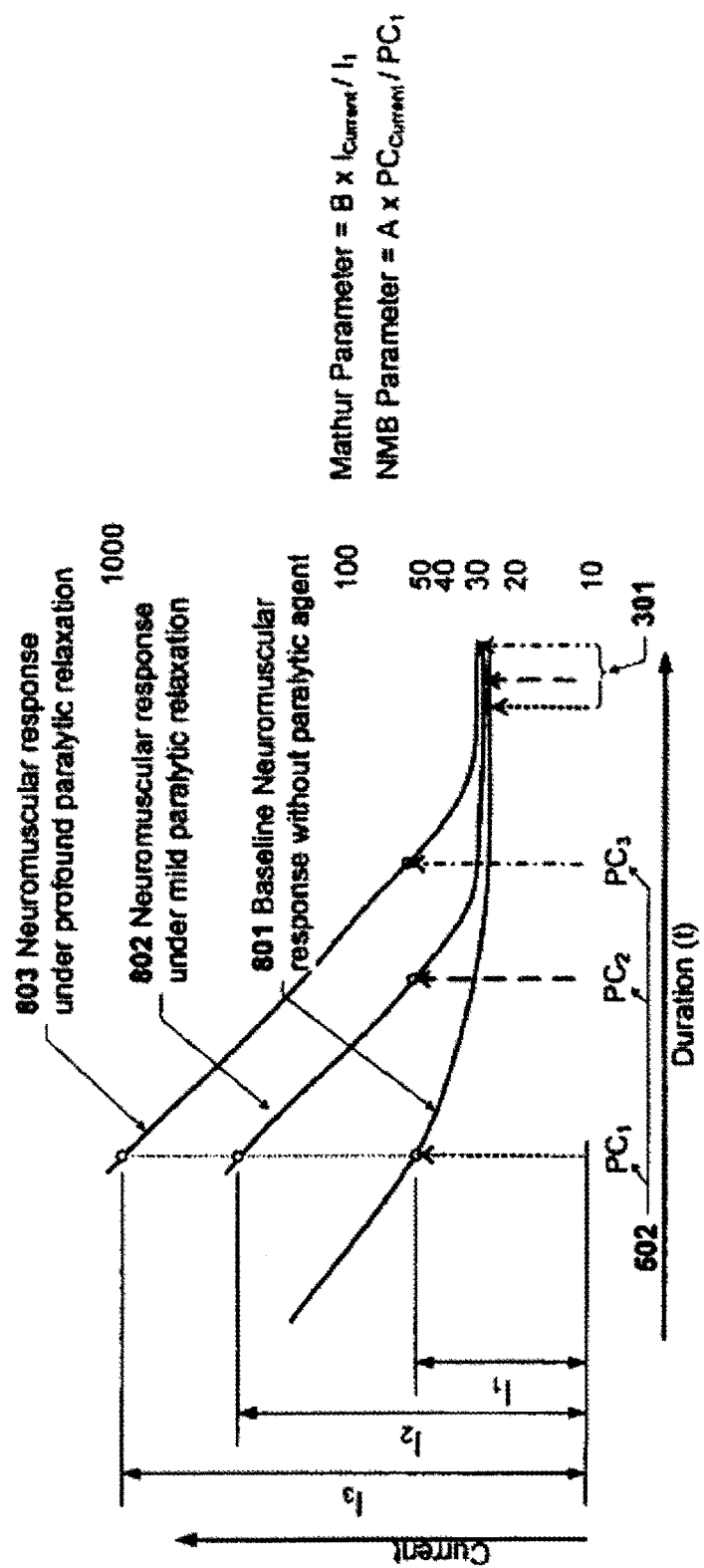
FIG. 8 illustrates an I-D curve according to some embodiments of the invention.

FIG. 8 illustrates an I-D curve according to some embodiments of the invention. Specifically, FIG. 8 shows an I-D curve corresponding to a live person (a patient) under various degrees of muscular relaxation due to paralytic NMBA. The system 100 of FIG. 1 can be used to measure chronaxie to determine the degree of NMB relaxation.

In FIG. 8, curve 801 is the I-D response of a muscle before the NMBA is administered. Curve 801 also corresponds to the neuromuscular response after full recovery from the effects of the NMBA. In contrast, curve 802 corresponds to the neuromuscular response under mild paralytic relaxation, while curve 803 corresponds to the neuromuscular response under profound paralytic relaxation.

Referring to FIG. 8, the curve 801 (corresponding to the patient's state before administering the NMBA) is used as a baseline. The Pseudo-chronaxie of the curve 801 is referred to as $PC_1$, and the current corresponding to $PC_1$ is referred to as $I_1$.

The patient's Pseudo-chronaxie can be measured in real-time to obtain a temporal Pseudo-chronaxievalue ($PC_{current}$) and a stimulus current ($I_{current}$) corresponding to $PC_{current}$. Next, an NMB parameter is determined based on the ratio between $PC_{current}$ and $PC_1$. The NMB parameter is a robust indicator of profoundness of muscle's paralytic relaxation, and is given by the following equation:

NMB parameter=$A*PC_{current}/PC_1$ where $A$ is a scaling factor

In some embodiments, the value of A may be one.

The NMB parameter can be interpreted as follows. When the value of the NMB parameter is approximately one, it means that the muscle has fully recovered to normal condition. When the value of the NMB parameter is greater than one, the NMB parameter can provide a quantitative measure of the degree of NMB. For example, the patient's muscle is in a mild paralytic relaxation regime when 4≥NMB parameter>1; moderate paralytic relaxation régime when 7≥NMB parameter>4; and profound paralytic relaxation regime when 10>NMB parameter>7.

Thus, the NMB Parameter can serve as a quantitative measure (based on Pseudo-chronaxie) of the patient's muscular relaxation under paralytic agent. Accordingly, the NMB parameter can provide an objective measure of the patient's response to paralytic agents in the medical procedure.

Figure 18:
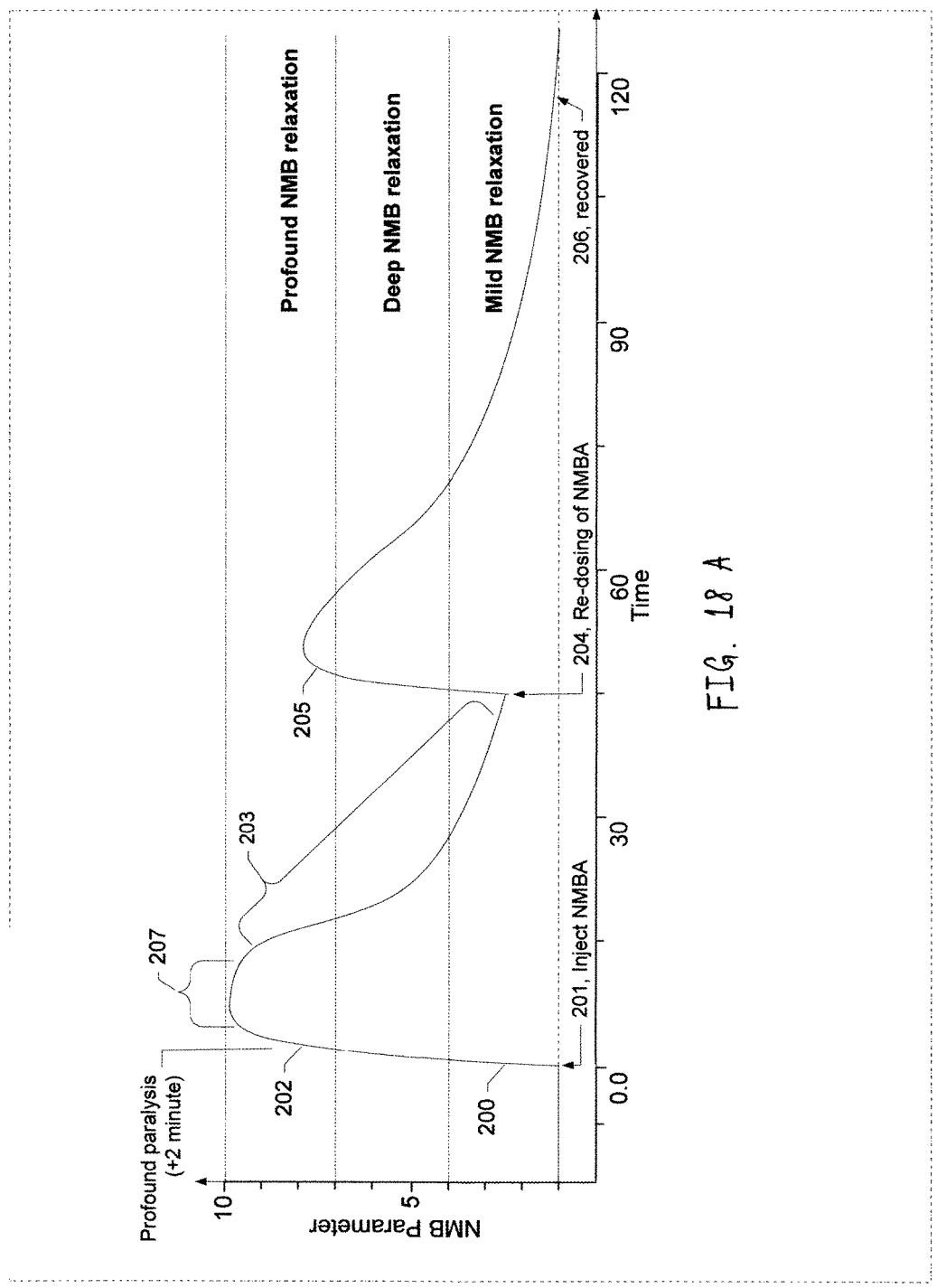
FIG. 18A shows the progression of anesthesia procedure and NMB parameter according to some embodiments of the invention.
FIG. 18B shows progression of the anesthesia procedure and the effect of NMBRA (E.g. Neostigmine) on a patient.

FIG. 18A shows the progression of anesthesia procedure and NMB parameter according to some embodiments of the invention. At the beginning of the anesthesia procedure, the NMB parameter is approximately equal to one. When NMB block medication (NMBA) is injected into the body (201), the NMB parameter rapidly rises to a regime of profound NMB relaxation (202). As the body (specifically the liver) metabolizes the NMBA, the NMB parameter starts to degrade (203) and drops to a mild NMB relaxation regime over time. The characteristic of rise time, hold time, and rate of decay is patient specific. Based on the rise time, hold time, and rate of decay, the NMB parameter decay characteristic for each patient can be modeled using different methods (e.g., calculating the set of coefficients of a polynomial equation). For example, when a predetermined dose of NMB block medication is injected into the patient's body, the decay rate can be modeled as an exponential decay constant based on curve section 203. The time taken to rise from 10% to 90% of the peak NMB parameter is modeled as the rise-time. The curve section 207 can be modeled as the 'hold-time,' which corresponds to the time the NMB parameter stays above 90% of the peak NMB parameter.

In some embodiments, by administering the initial NMBA dose in two portions, further insights to a patient's sensitivity to NMBA can be obtained. The first portion of the NMBA dose raises the NMB parameter to a level between 4 and 9, and allows the patient's response to moderate dose of NMBA to be more accurately modeled. This can be particularly useful when re-dosing the patient, in which the aim of the re-dosing is to extend the NMBA induced paralysis by a desired time, without incurring the risk of over-increasing the time to recover from NMBA. The second portion of the NMBA dose is shortly administered after the patient's NMB parameter profile is captured, so as to extract different modal parameters.

With reference to FIG. 18A, the re-dosing of NMBA is performed (204) to partially increase the NMB relaxation (205). At 206, the NMB parameter has dropped back close to one and the muscle is fully recovered from the effect of the NMBA drug.

Figure 18B:
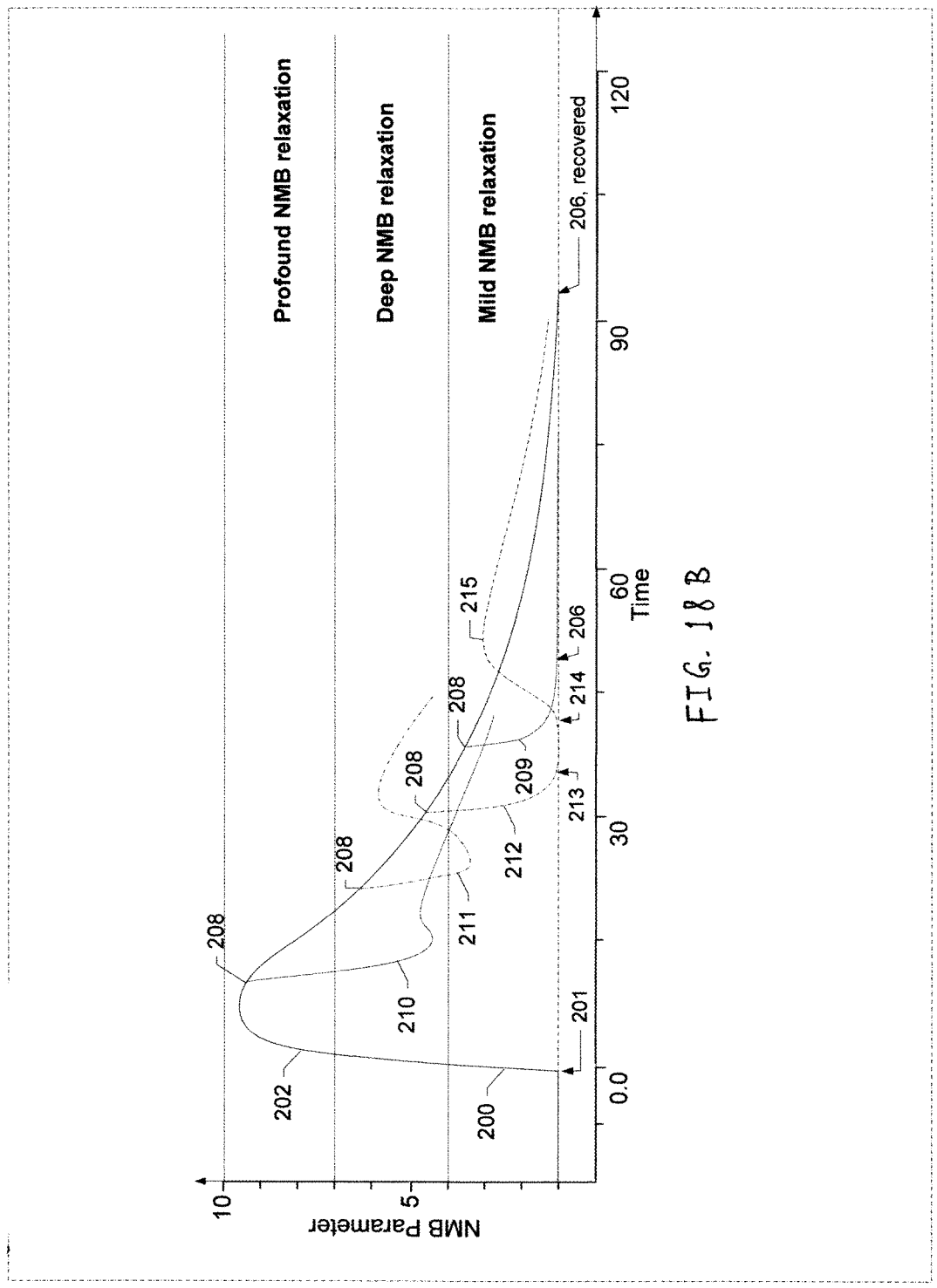

FIG. 18B shows progression of the anesthesia procedure and the effect of NMBRA (e.g. Neostigmine) on a patient. In FIG. 18B, the curve 209 shows the NMB parameter curve modification when a correct dose of NMBRA is administered at a time when the patient's NMB parameter is in the mild-NMB relaxation regime. The patient's NMB parameter quickly decays to a stable value close to the value of about one (206), corresponding to patient having fully recovered from effects of NMBA.

Referring to FIG. 18B, curve 210 shows the NMB parameter curve modification when a correct dose of NMBRA is administered, specifically at a time when the patient's muscle is profoundly relaxed due to NMBA. The patient's NMB parameter quickly decays but fails to reach anywhere close to 1. In this example, the NMB parameter levels out at around 4.5 and as the NMBRA is metabolized, the NMB parameter starts to decay slowly under the effect of residual NMBA.

As further shown in FIG. 18B, curve 211 shows the NMB parameter curve modification when an excessive dose of NMBRA is administered, specifically at a time when patient's muscle is profoundly relaxed due to NMBA and the patient's specific medical condition causing recurarization. Initially, the patient's NMB parameter quickly drops after administration of the NMBRA. However, due to recurarization, the NMB becomes more profound and the NMB parameter subsequently rises to a level that is even higher than in the case corresponding to un-mitigated NMB decay (without any NMBRA). This further increases the time it takes for the patient to recover from NMBA, and is counterproductive to the objective of administering NMBRA. However, if the patient's specific medical condition does not cause recurarization, the curve shape will be similar to curve 210.

As a further example, curve 212 of FIG. 18B shows the dangerous NMB parameter curve modification, caused by administering an excessive dose of NMBRA when the patient's muscle is moderately relaxed due to NMBA and the patient's specific medical condition causing recurarization. Initially, the patient's NMB parameter quickly drops to a healthy value of about one after administration of the NMBRA. However, due to recurarization, the NMB becomes more profound and the NMB parameter rises to a level that is even higher than the case of an un-mitigated NMB decay (without any NMBRA). This condition (high NMB parameter level) can be deadly for the patient, particularly if the life support system is removed and the patient is revived from anesthesia. Specifically, the recurarization induces NMB (214), thereby paralyzing the patient's vital muscles as a result of the increased NMB parameter value (215).

The system 100 according to some embodiments can measure the NMB parameter during the anesthesia procedure, which provides one or more of the following advantages over the existing methods/systems of detecting paralysis state. First, the system 100 can accurately assess patient's degree of NMB relaxation in real-time. Second, the system 100 can accurately assess appropriate dosage of NMBRA, and when it is appropriate to administer and its actual efficacy. Third, the system 100 can accurately assess appropriate quantum of dosage of NMBRA to extend the duration when the muscle will continue to be relaxed by a specific desired duration, such that patient can quickly recover from the effect of NMBA induced paralysis. Fourth, the system 100 can determine when the patient has fully recovered from the effect of NMBA, so that it is safe to remove life support system.

As mentioned previously in FIG. 8, the curve 801 (corresponding to the patient's state before administering the NMBA) is used as a baseline. The Pseudo-chronaxie of the curve 801 is referred to as $PC_1$, and the current corresponding to $PC_1$ is referred to as $I_1$. The patient's Pseudo-chronaxie can be measured in real-time to obtain a temporal Pseudo-chronaxie value ($PC_{current}$) and a stimulus current ($I_{current}$) corresponding to $PC_{current}$. The NMB parameter is determined based on the ratio between $PC_{current}$ and $PC_1$, and is a robust indicator of profoundness of muscle's paralytic relaxation.

Similarly, the ratio between $I_{current}$ and $I_1$ can also be a robust indicator of profoundness of muscle's paralytic relaxation. This ratio can be parameterized by the "Mathur parameter." The Mathur parameter can provide an objective measure of the patient's response to paralytic agents in the medical procedure, and is given by the following equation:

Mathur parameter=$B*I_{current}/I_1$ where $B$ is a scaling factor

In some embodiments, the value of B may be one.

Thus, the Mathur Parameter is a quantitative measure of the patient's muscular relaxation under paralytic agent, and is based on the electric current ratio at a particular time duration corresponding to Baseline Chronaxie ($PC_1$).

Since the Mathur parameter behaves similar to the NMB parameter, the Mathur parameter can also be applied to assess the degree of a muscle's NMB.

FIG. 2A shows an embodiment of the sensing system 102. The sensing system 102 includes one or more motion sensor(s) 002 and stimulus electrodes 001.

As shown in FIG. 2A, motion sensor(s) 002 are mounted near the apex of the thumb 005 to measure the physiological response of the thumb muscle 006. The thumb muscle 006 is generally used to assess a patient's NMB, because the thumb muscle's NMB behavior is similar to that required for vital muscle groups in the thorax that allow breathing. In addition to the thumb muscle, the sensing system 102 can also measure the physiological response of other muscle groups.

The stimulus electrodes 001 provide an electrical stimulus. As shown in FIG. 2A, the electrodes 001 are mounted at an appropriate place near the wrist, to send an electrical stimulus to the nerves 004 to excite the target muscle 006.

When the target muscle 006 is stimulated by the stimulus applied by the electrodes 001, the target muscle 006 moves the thumb in the direction 007 as shown in FIG. 2A. The thumb movement is measured by motion sensors 002 that measure inertial movement. In some other embodiments, other methods of measurement (e.g. using strain-gauge, inductive pickup, etc.) can be used to measure the relative movement between body parts.

FIG. 2B shows the physiological movement and sensor frame of the sensing system 102 in FIG. 2A.

In FIG. 2B, the sensing system 102 includes sensors that can measure linear or angular inertial motion in one or more axes. The sensor body axes 008 can be used as a reference frame on its own, by taking its initial position before application of stimulus as the reference frame. The sensors frame 008 can also be transformed to an external frame (e.g., aligned with local vertical, and horizontal azimuthal plane) or inertial frame. When stimulated, the thumb twitches and moves along the path 007. This results in angular movement 009 as well as linear movement 007.

In some embodiments, the sensors in the sensing system 102 can include rate-gyroscopes. Rate-gyroscopes can be used as sensors to measure angular movement. Advantages of angular movement measurement include easy transformation to sensor axes, immunity to kinematic noise and linear acceleration due to gravity, and direct detection by sensors that detect singular movement.

In some embodiments, the sensors in the sensing system 102 can include linear accelerometers.

In some preferred embodiments, the sensors in the sensing system 102 can include both linear and angular sensors. The linear and angular sensors can be used for cross verification, redundancy, greater measurement accuracy, so as to obtain a higher confidence level of the data.

In some embodiments, the sensors in the sensing system 102 can include motion sensors 002 using two or three orthogonal rate-gyroscopes to provide a signal corresponding to angular acceleration along the axes where twitch motion is pronounced. Since the thumb movement is hinged at the base of the thumb, the orthogonal rate-gyroscopes provide robust measurement of thumb movement with respect to the base of the palm. This arrangement is immune to vibration caused by movement of a patient in a gurney, wheeled ambulance, or helicopter ambulance, because these vibrations are largely linear in nature and do not result in significant thumb rotation. Since the human thumb has two degrees of freedom (angular), a minimum of two orthogonal rate-gyros is typically sufficient to measure thumb movement. In some cases, useful functionality may be obtained using one rate-gyro, provided the axis of the rate-gyro is properly aligned with expected thumb movement. Nevertheless, the three gyro arrangement is generally preferred because of the easy availability of the gyros and the ability to provide proper inertial frame for an Inertial Measurement Unit (IMU) style measurement package.

In using sensors to measure acceleration, math operations (such as frame translation and integration) allow realization of velocity and displacement information. Acceleration is integrated over time to provide velocity information (i.e. the speed at which thumb moved), and velocity is integrated over time to provide displacement information (i.e. the distance the thumb has moved). This is true for angular acceleration. Frame translation can be more robust if three orthogonally mounted angular sensors (e.g. rate-gyros) are also available in the sensor package.

For linear acceleration, accurate velocity and displacement information can be obtained as long as the constant bias due to acceleration due to gravity is compensated. When the thumb is not being stimulated, it is relatively easy to determine gravity's contribution on all three linear accelerometers, and the sensor's axis frame with respect to the direction of gravity. Thus, the acceleration bias due to gravity from the accelerometer data can be easily negated.

In some embodiments, the sensors in the sensing system 102 can include motion sensors comprising three orthogonal accelerometers, which provide a signal corresponding to the acceleration along each sensor's respective axis of sensitivity. Since the motion sensor is (temporarily) glued to the thumb surface, one can resolve thumb movement after subtracting the bias due to acceleration due to gravity. The bias is best measured a short time before the stimulus to the nerve is applied.

In some embodiments, the sensors in the sensing system 102 can include motion sensors comprising three rate-gyro accelerometers and three orthogonal accelerometers, thus providing all the information necessary to compute angular as well as linear displacement of the thumb. Computation methods similar to that employed in Strap-down Inertial Navigation System can be used to get movement information. This arrangement provides higher sensitivity, confidence and easier computation, as well as immunity to ambient vibration.

In some embodiments, the sensors in the sensing system 102 can include sensors (such as strain-gauge, etc.) that provide displacement information. Velocity can be obtained by differentiating the displacement with respect to time, and acceleration could be further obtained by differentiating the velocity with respect to time.

In some embodiments, the sensors in the sensing system 102 can include other types of sensors (e.g. magnet & coil pickup) that provide velocity information. Displacement can be obtained by integrating velocity with respect to time, and acceleration can be obtained by differentiating the velocity with respect to time.

Figure 6:
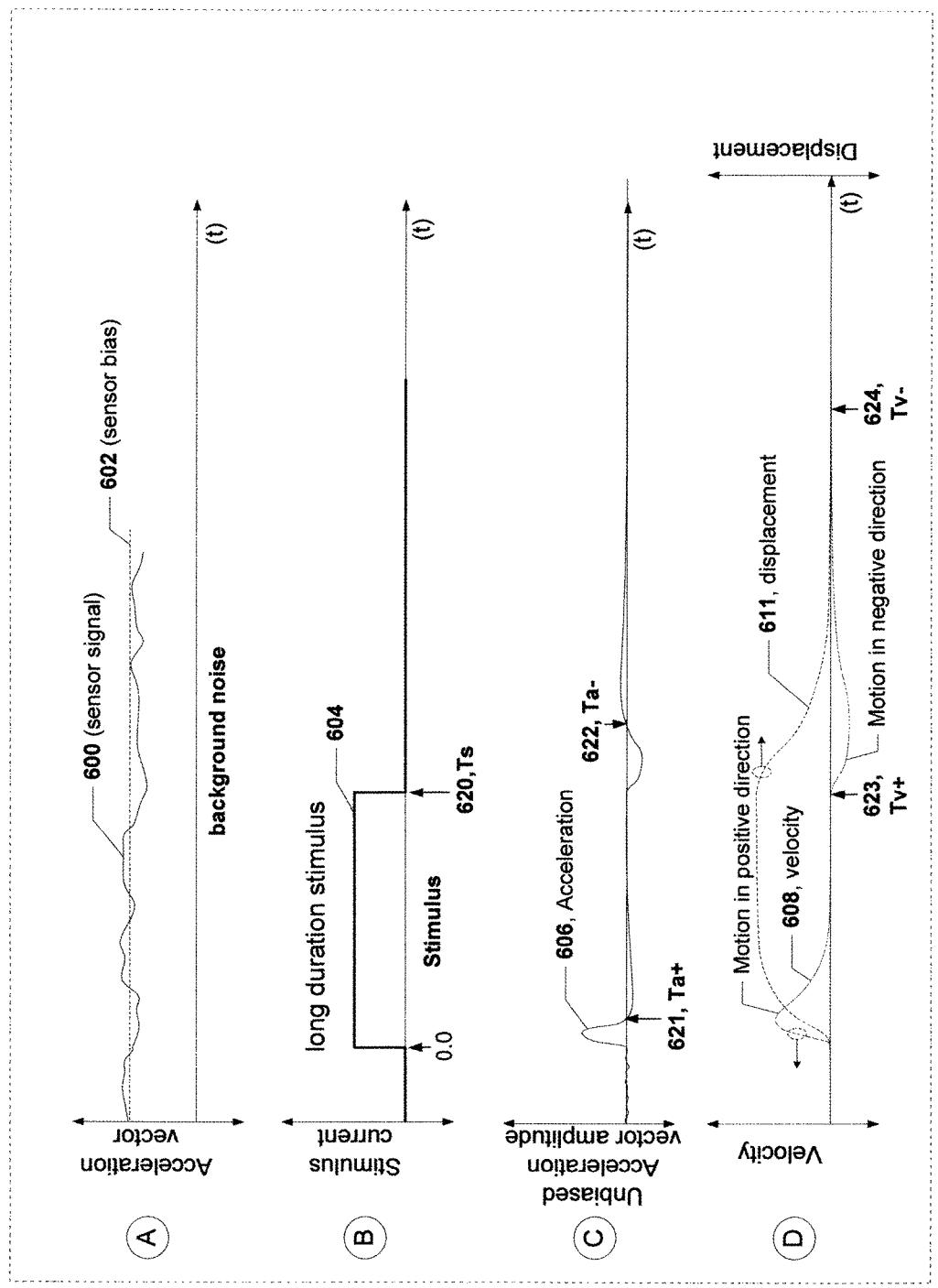
FIGS. 6 and 7 illustrate kinematic signals corresponding to some embodiments of the invention using linear or angular acceleration sensors.
Figure 7:
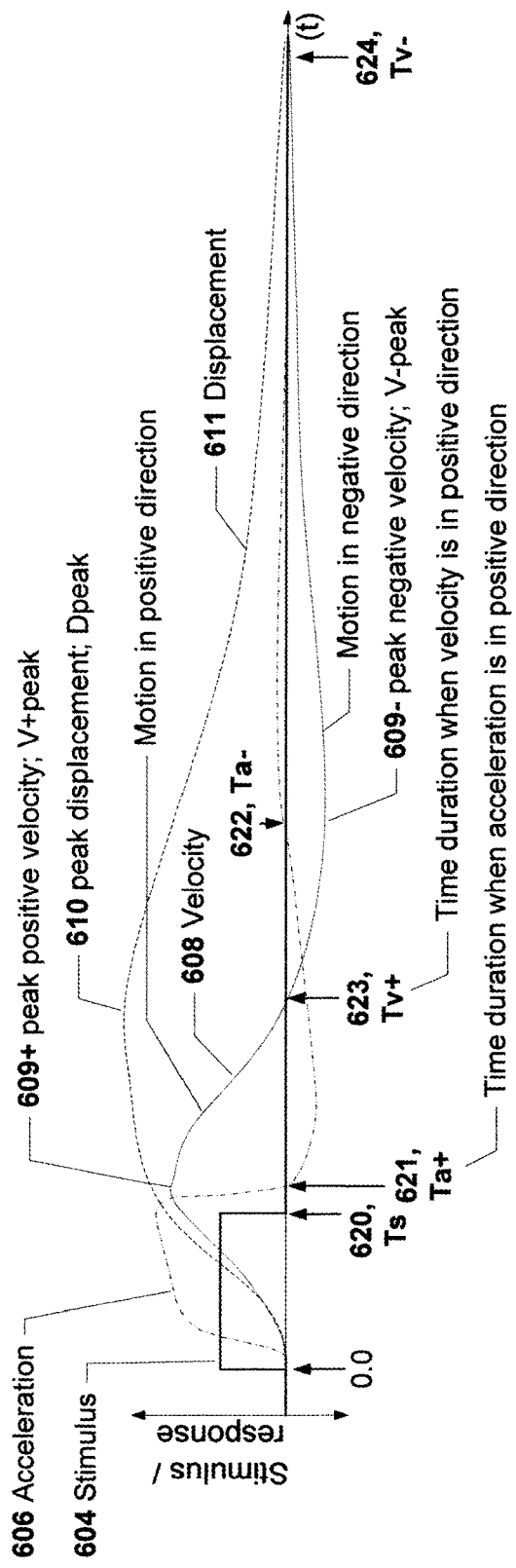

FIGS. 6 and 7 illustrate kinematic signals corresponding to some embodiments of the invention using angular acceleration sensors. It should be noted that linear sensors or IMU-based sensors can also be used to detect kinematic signals.

With reference to FIG. 6, the sensor signal 600 in Graph A shows the computed acceleration vector magnitude (i.e. the vector sum of acceleration component from the orthogonally mounted sensors) due to electronic noise of sensor as well as ambient physical (e.g. mechanical) background vibration. Graph A also shows a sensor bias 602.

Graph B shows a strong stimulus 604 applied to a thumb for long duration (e.g. few hundred milliseconds). The Stimulus period 620 (Ts) is long enough such that muscle reaches the final position and is at equilibrium before the stimulus ends.

Graph C shows acceleration vector output 606 as the thumb moves fully in response to the long duration stimulus and after the stimulus is removed. The shown acceleration vector has bias removed. Ta+ (621) is the time when acceleration in the positive direction ends during muscle contraction. Ta− (622) is the time when acceleration in the negative direction ends during muscle relaxation.

Graph D shows the computed velocity 608 and displacement 611 obtained by integrating the acceleration signal over time, and by integrating the velocity over time, respectively. In Graph D, the initial velocity is assumed to be zero, and initial displacement is used as datum. Tv+ (623) is the time when velocity in positive direction ends during muscle contraction. Tv− (624) is the time when velocity in negative direction ends during muscle relaxation.

The 'Typical short-stimulus, kinematic response and parameters' in FIG. 7 are similar to the parameters in FIG. 6. In contrast to FIG. 6, FIG. 7 is for a relatively short duration stimulus period (i.e. the duration significantly less than a few hundred milliseconds). FIG. 7 shows the typical kinematic response, acceleration signal 606, the computed velocity 608, and displacement 611, generated by integrating the acceleration signal once and twice with respect to time respectively. In FIG. 7, the initial velocity is assumed to be zero, and initial displacement is used as datum.

FIG. 7 also shows key parameters that can be used to model the twitch of the thumb. The parameters are applicable for both angular and linear types of motion sensors. The parameters are collected as a data structure and henceforth referred as Twitch Data Set (TDS). The TDS includes, for example:

a) Stim_I: Stimulus Current
b) Stim_Period: Period of time 620 (Ts) when 'Stim_I' is applied
c) Ta+: Time 621 when acceleration transitions from positive direction to negative direction. Velocity reaches its peak value 609+ (V+peak) at this moment.
d) Ta−: Time 622 when acceleration transitions from negative direction to positive direction. Velocity reaches its peak negative value 609− (V−peak) at this moment.
e) Tv+: Time 623 when velocity transitions from positive direction to negative direction. Displacement reaches its peak value 610 (Dpeak) at this moment.
f) Tv−: Time 624 when negative velocity decays down to ≤(NfMultiplier×V−peak), where:
   i) 0.01≤NfMultiplier≤0.3
   ii) NfMultiplier is a threshold reference that is dependent on sensor sensitivity, noise floor and detection margin.
g) Amavgp: Acceleration, peak of the moving average, in positive direction (typical window size 10 mSec)
h) Aavg: Average acceleration from 0 to Ta+
i) Vmavgp: Velocity, peak of the moving average, in positive direction (typical window size 10 mSec)
j) Vavg: Average acceleration from 0 to Tv+
k) Dmavgp: Displacement, peak of the moving average, in positive direction (typical window size 10 mSec).

FIG. 6 also shows key event markers (621 Ta+, 622 Ta−, 623Tv+, 624Tv−) and TDS parameters that are collected to model the twitch of the thumb.

Figure 9:
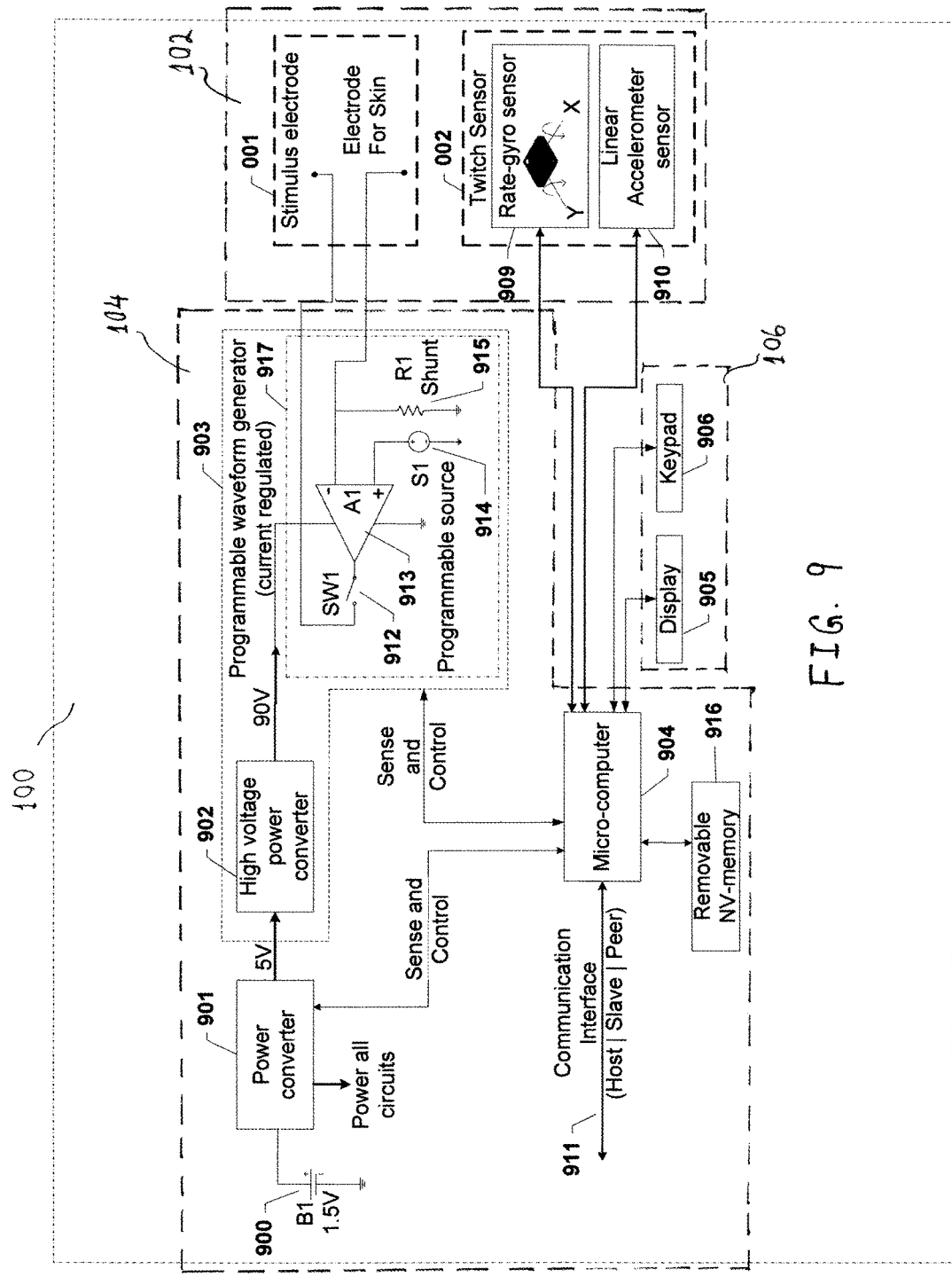
FIG. 9 shows a block diagram of a system 100 according to some embodiments of the invention.

FIG. 9 shows a block diagram of a system 100 according to some embodiments of the invention. The system 100 of FIG. 9 can be used to quantitatively measure a patient's NMB.

Referring to FIG. 9, the system 100 includes a sensing system 102, paralysis assessment system 104, and I/O devices 106.

The paralysis assessment system 104 includes a micro-computer 904. The micro-computer 904 can be a computer that runs software to implement necessary, communication, and control and input-output functions to implement the desired functionality. The micro-computer 904 can have a built-in self-test mode that verifies critical voltages, current, and pulse sequences, which gives the micro-computer 904 high operational reliability and safety.

The micro-computer 904 can further include a CPU (Central Processing Unit), a Main memory (RAM), a non-volatile memory to store patients' data and operating program and configuration information, and Input Output peripherals. The non-volatile memory can include, for example, removable non-volatile memory 916 (e.g., Flash memory) to store patients' data and for easy transfer of information.

The paralysis assessment system 104 also includes a Power Converter and Management circuit 901 that converts raw input power from battery 901 into regulated voltage power to operate the electronics in the paralysis assessment system 104. The Micro-computer 904 can be configured to monitor and manage the Power Converter and Management circuit 901 for proper operation and to conserve energy.

The paralysis assessment system 104 also includes a Programmable Waveform generator 903 that can generate an electrical stimulus that is applied to stimulus electrodes 001. The Programmable Waveform generator 903 can include a High voltage power converter 902 and a Switchable Current Regulator 917.

The high voltage power converter 902 can convert the low voltage from power converter 901 to generate a high voltage ranging from about 40 volts to 90 volts, with the necessary power to produce required neuro-muscular stimulus 604.

The Switchable Current Regulator 917 draws high voltage power from High-voltage power converter 902, and generates a controlled current (with a set voltage compliance) waveform as stimulus per Micro-computer instructions. The output of the Switchable Current Regulator 917 is connected to stimulus electrode 001. The Switchable Current Regulator 917 also measures the actual current output and reports the output to the micro-computer 904.

The Switchable Current Regulator 917 includes a programmable voltage source S1 (914), whose set-point can be quickly set by the Micro-computer 904. The set-point is a scaled representation of the desired output current.

The Switchable Current Regulator 917 further includes a current regulator whose output voltage compliance is quite high (~90 Volt) that can be rapidly turned on and off.

The current regulator includes an op-amp 913 configured as a current regulator. The non-inverting input of the op-amp 913 is connected to S1 (914) to define the current regulator's set-point. The inverting input of op-amp is connected to current shunt R1 (915) that measure the actual current flowing into stimulus electrode 001. The output of the high-voltage op-amp is connected to one of stimulus electrodes 001.

The current regulator also includes a switch 912. The circuit is configured with a switch 912 in a way such that micro-controller can rapidly turn the current regulator on or off. When the current regulator is off, there is no output stimulus, and when turned on the output current is proportional to the programmable voltage source S1 (914).

The paralysis assessment system 104 further includes External Communication Interface 911. The paralysis assessment system 104 can interface with an external system through communication interface 911 connected to its micro-computer 904. The communication interface 911 provides a means to integrate it other system as a peer, host or slave. (e.g. Hospital Patient Monitoring System, Electronic Medical Record system, Automated I-V Medicine Dispenser etc.). One can choose from a range of communication interface (e.g. serial, USB, I2C, LAN) and protocols (e.g. HTTP, HTTPS, RMI, SOAP, XML etc.) protocols.

Next, the sensing system 102 in FIG. 9 will be described. The sensing system 102 includes stimulus electrodes 001 and Twitch Sensor 002.

The stimulus electrode 001 provides electrical connectivity to body parts, to allow the paralysis assessment system 104 to excite the targeted neuro-muscle.

The Twitch Sensor 002 includes one or more rate-gyro sensor(s) 909 and linear accelerometer sensor(s) 910. The Twitch Sensor 002 is mounted on a body part to measure physical movement due to twitching of target muscle. As shown in FIG. 9, more than one type of sensors may be used at the same time to improve accuracy (e.g. higher signal to noise ratio) and robustness. The Twitch sensor communicates with the Micro-computer 904 via a wired connection. To conserve battery energy, the Twitch sensor 002 can be powered only when needed.

In some embodiments, the Twitch sensor 002 can be wirelessly connected to Micro-computer 904, in which case a local small battery powers the Twitch sensor 002 and another micro-computer may be employed to make it self contained unit. (See, e.g. FIGS. 10, 11, 12, 15, and 16).

As previously mentioned, the sensor transducer element in the Twitch Sensor 002 can be chosen from one or more of the following sensors (non-exhaustive list) located along one or more orthogonal axis: (1) Rate Gyro sensors (measure angular acceleration); (2) Linear accelerometers (measure linear acceleration); (3) Vibration sensors; (4) Piezo sensors; (5) Magnetic coil sensors; or (6) Strain gauges.

Next, the I/O device 106 in FIG. 9 will be described. The I/O device 106 includes Display 905 and Keypad 906.

The Keypad 906 is connected to Micro-computer 904 and provides a convenient user interface.

The Display 905 can be connected to Micro-computer 904. The Micro-computer 904's operating program can display appropriate information via display 905 to the user. The Display 905 may use current display technologies (e.g. LED, LCD, etc.) to provide a Graphical display or simple Character based display. The Display 905 may have an integrated audio interface (e.g. speaker, buzzer) with necessary audio synthesis capability. The Display 905 can also be configured to show graphical charts of data, the patient's name, hospital record number, the stimulus characteristics, and the measured patient's response.

Figure 10:
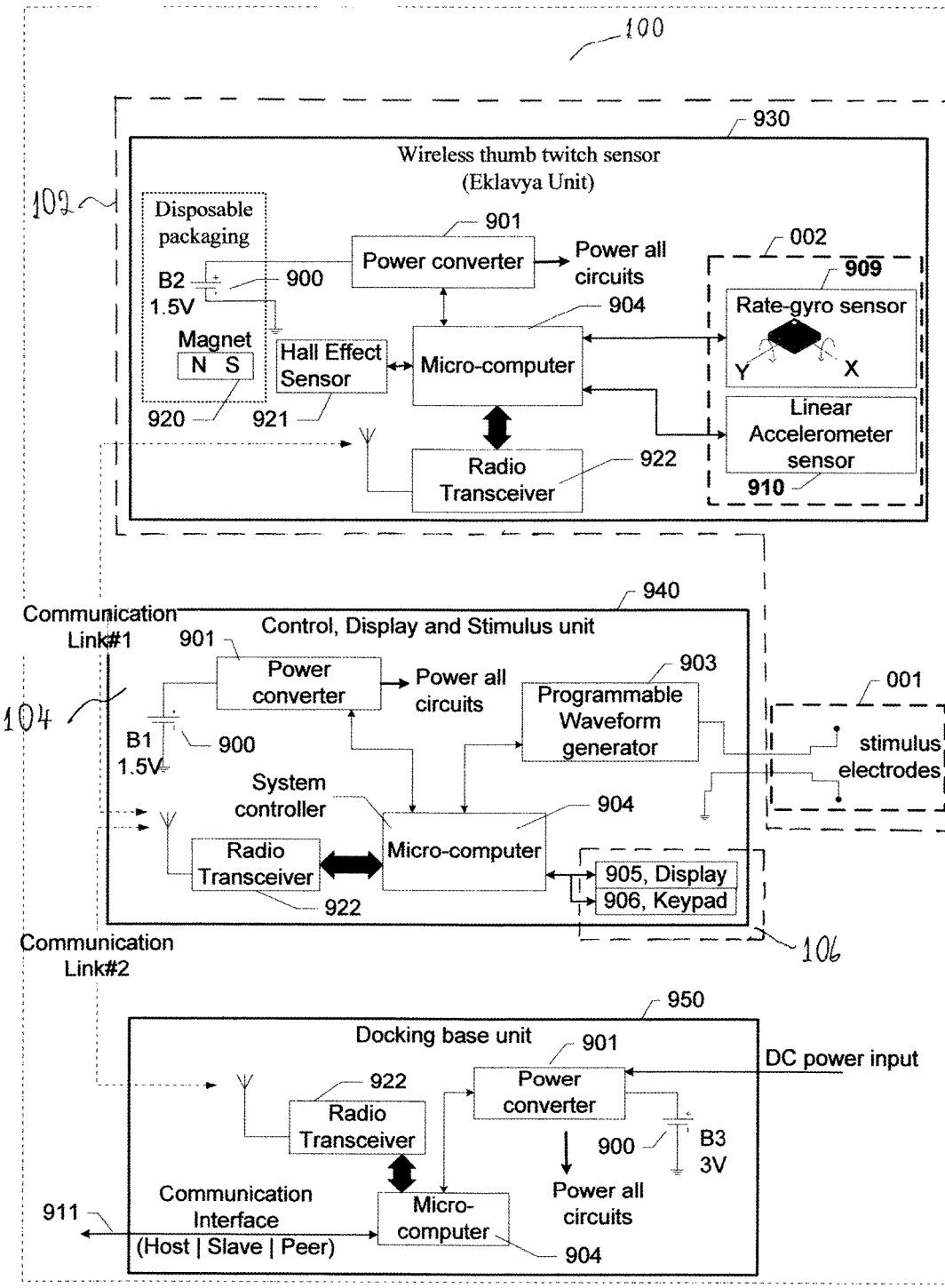
FIG. 10 shows a block diagram of another embodiment of the system 100 of FIG. 9.

FIG. 10 shows a block diagram of another embodiment of the system 100 of FIG. 9. The key difference between FIGS. 9 and 10 is that the sensing system 102 in FIG. 9 is wired to the paralysis assessment system 104, while the sensing system 102 in FIG. 10 is wireless.

In FIG. 10, the system 100 includes sensing system 102, paralysis assessment system 104, and I/O device 106. The system 100 further includes a Docking base unit 950. In the embodiment shown in FIG. 10, the sensing system 102 includes Wireless thumb twitch sensor 930, and the paralysis assessment system 104 includes Control, display and Stimulus unit 940.

As shown in FIG. 10, the Wireless thumb twitch sensor 930 includes Twitch Sensor 002 of FIG. 9. The Wireless thumb twitch sensor 930 further includes a power converter 901, micro-computer 904, and radio transceiver 922. The data from the Twitch Sensor 002 is sent to the micro-computer 904 (within Wireless thumb twitch sensor 930). In some embodiments, the Wireless thumb twitch sensor 930 can communicate with the Micro-computer 904 (in the Control, display and stimulus unit 940) either via wired connection or wireless connection.

One type of sensor element that is found to be very robust for thumb unit application is the "Rate-gyro" sensor in single or multi-axis configuration. The human thumb only has two rotational degree of freedom (no rotational freedom along the length of thumb). Accordingly, some embodiments of the Twitch Sensor 002 of FIG. 9 include a two axis Rate-Gyro sensor.

In some embodiments, more than one type of sensors may be used in the sensing system 102 at the same time to reduce noise and robustness. For example, in some embodiments, the sensing system 102 can include both linear and angular acceleration sensor types that are used at the same time.

The Control, display and stimulus unit 940 can include a hand-held device operating on AAA battery. The Control, display and stimulus unit 940 can include a Micro-computer 904 that executes an operating program for necessary control, sequencing, display and user input. The Micro-computer 904 can remotely control the other two sub-system via communication interface link #1 and link #2 provided by Radio Transceiver 922.

The Control, display and stimulus unit 940 can include a Programmable waveform generator 903. The Programmable waveform generator 903 connects to stimulus electrode 001. The electrical pulses are transmitted to the patient through a wire, which has a minimum of two pads/electrodes that are adhesively attached to the patient's skin and that excite the Ulnar nerve underneath the skin.

The Control, display and stimulus unit 940 can include Power converter 901, which converts battery power to regulated voltage suitable for powering all circuits in the sub-system.

The Control, display and stimulus unit 940 can include Radio Transceiver 922, which provides low power, short range communication connectivity with Wireless thumb twitch sensor 930 and Docking base unit 950.

Similar to FIG. 9, the I/O device 106 in FIG. 10 includes Display 905 and a Keypad 906.

In FIG. 10, the docking base unit 950 can provide a place to keep the sub-system secure while not in use. The docking base unit 950 can communicate to Control, display and stimulus unit 940 via radio transceiver 922. The docking base unit 950 can provide connectivity to other systems via communication interface 911. For rechargeable battery version of Control, display and stimulus unit 940, the docking base unit 950 can provide recharging power. In some embodiments, the docking base unit 950 can be an optional sub-system of system 100.

Figure 11:
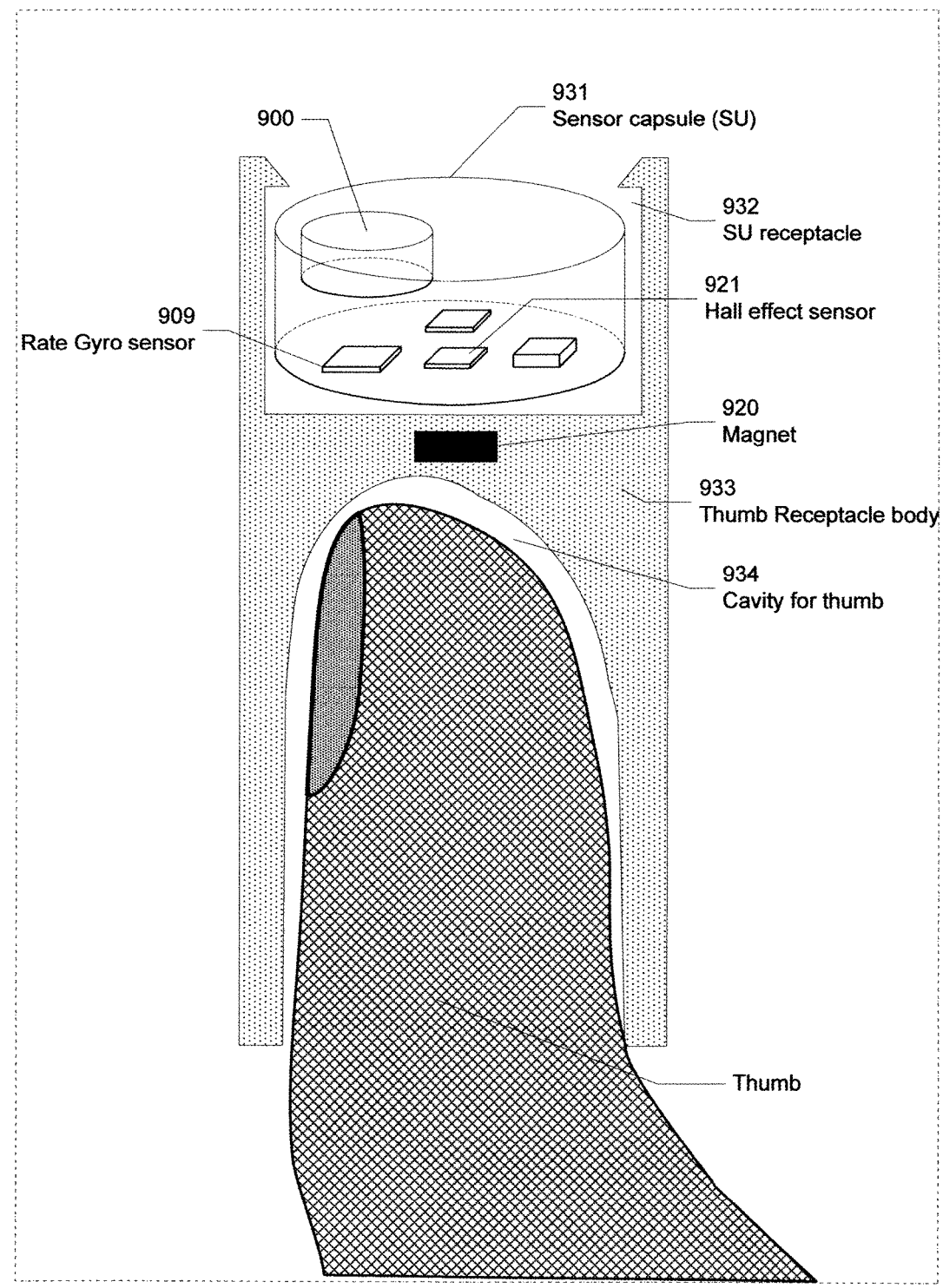
FIGS. 11 and 12 show examples of different ways in which the thumb twitch sensor 930 of FIG. 10 can be packaged.
Figure 12:
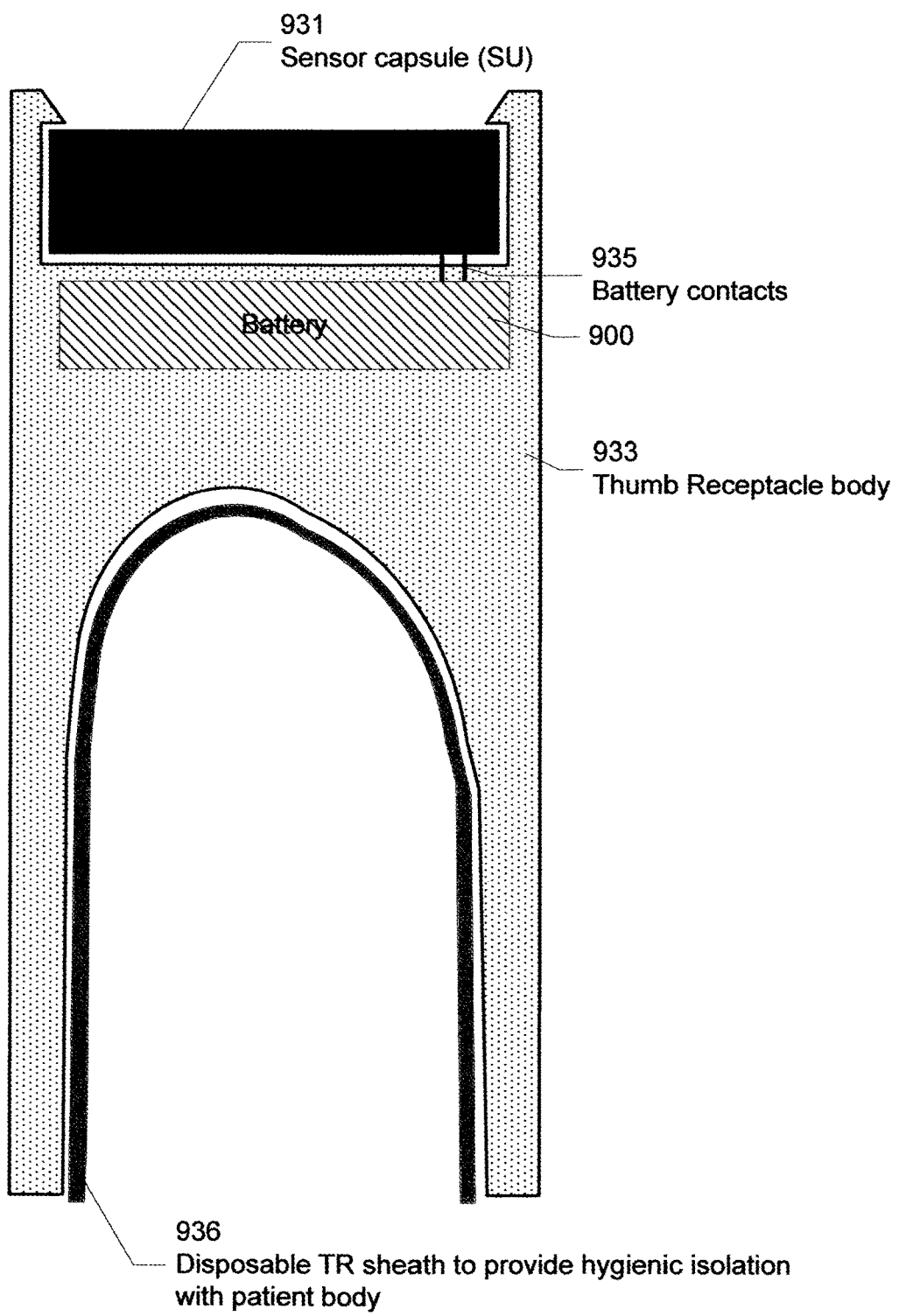

FIGS. 11 and 12 show examples of different ways in which the thumb twitch sensor 930 of FIG. 10 can be packaged.

As shown in FIG. 11, the Wireless thumb twitch sensor 930 includes a Sensor capsule (SU) 931, receptacles cavity 932, Hall effect sensor 921, magnet 920, thumb receptacle body 933, cavity 934, rate-gyro sensor 909, and battery 900.

The thumb receptacle body 933 provides a cavity 934 to fit the thumb and also a receptacles cavity 932 that allows a Sensor capsule (SU) 931 to snap in. In some embodiments, the thumb receptacle body 933 can have an embedded magnet 920. The unit's hall sensor 921 can sense it has been snapped into receptacle 920 by sensing magnetic field of embedded magnet 920.

The SU 931 is powered by a small battery 900. The battery 900 could be packaged in SU 931 as shown in FIG. 11. In some embodiments, the battery 900 can be a part of the thumb receptacle 933.

The SU 931 is paired with a specific Control, display and stimulus unit 940, and acts as a slave to it. Robust pairing is achieved by requiring cryptographic handshake.

The SU 931 houses electronics and sensors corresponding to thumb twitch sensor 930 of FIG. 10.

The SU 931 can include a Micro-computer 904 that executes an operating program for necessary control, sequencing and communication with Control, display and stimulus unit 940. It executes command requests from Control, display and stimulus unit 940.

The SU 931 can include a Radio Transceiver 922, which provides low power, short range communication connectivity with Control, display and stimulus unit 940.

The SU 931 can include sensor 002, which comprises the motion sensors previously described. The sensor 002 provides multi-axis response of the thumb twitching under electrical stimulus. The sensor 002 may be attached to a separable plastic housing 933, or a sheath 936 that can be disposed off (FIGS. 11 and 12).

The SU 931 can include Power converter 901, which converts battery power to regulated voltage suitable for powering all circuits in the sub-system.

The SU 931 can include Hall effect sensor 921. When the sensor capsule is inserted in the disposable thumb cap 934 that has a magnet 920 embedded in it, the Hall sensor 921 will be triggered. The Hall sensor 921 can thus automatically determine whether to turn on power to SU 931.

Referring to FIG. 12, a disposable thumb-receptacle sheath 936 lines the thumb cavity 934 for comfort and also provides hygiene isolation.

Figure 13:
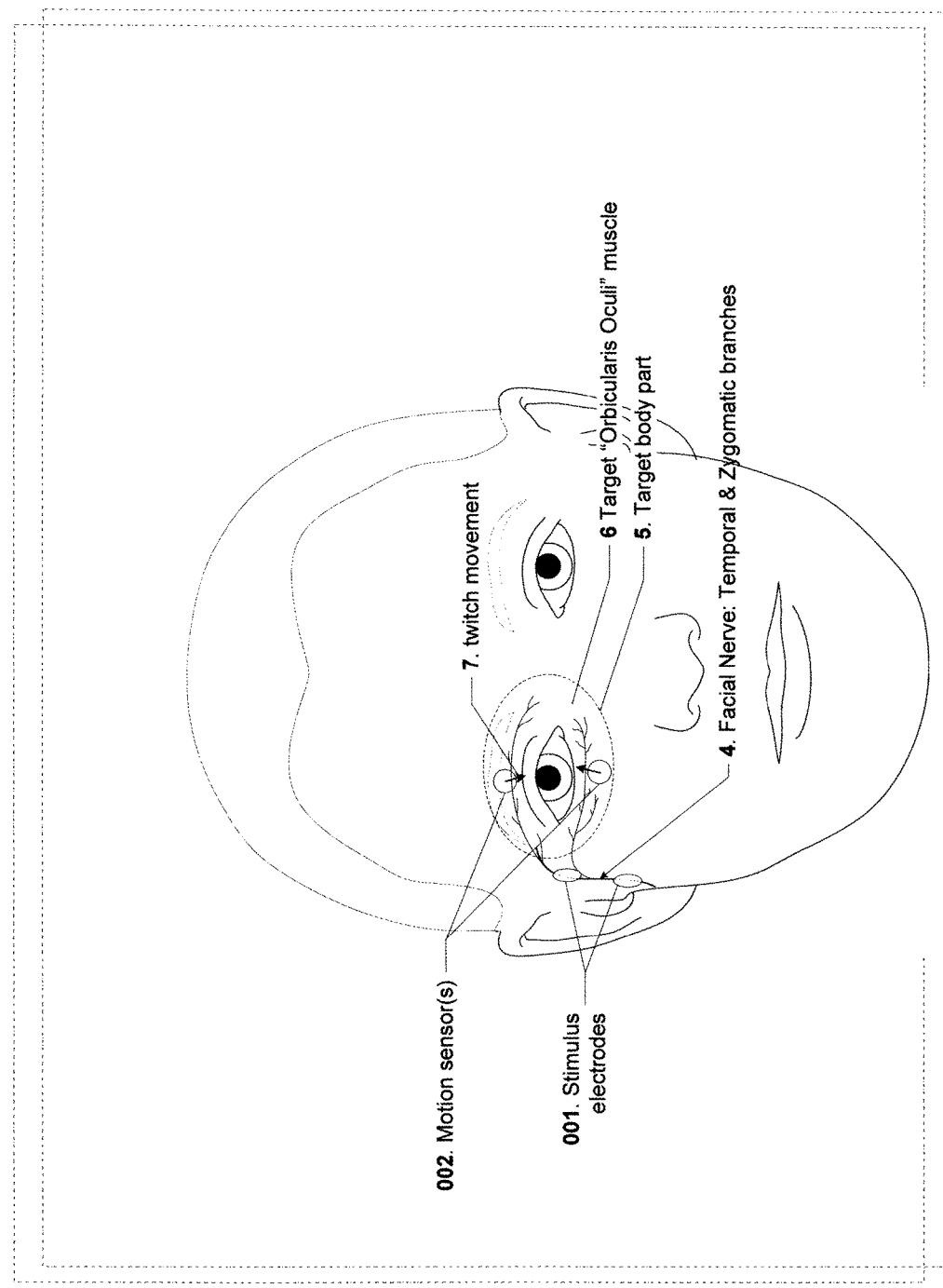
FIG. 13 shows how the teachings of the invention can be applied to other muscle groups besides the thumb.

The teachings of the invention can be applied to other muscle groups besides the thumb. In FIG. 13, the target muscle 6 is "Orbicularis Oculi", and the nerves 4 for the target muscles are the Temporal & Zygomatic branches of the 'Facial Nerve'. Stimulus electrodes 001 can be used to stimulate the Orbicularis Oculi muscle, and motion sensors 002 can be used to sense the eye-lid response to the stimulus.

FIGS. 14, 15, 16, and 17 show different embodiments in which the sensing system is targeted at the eye-lid of a patient.

Figure 14:
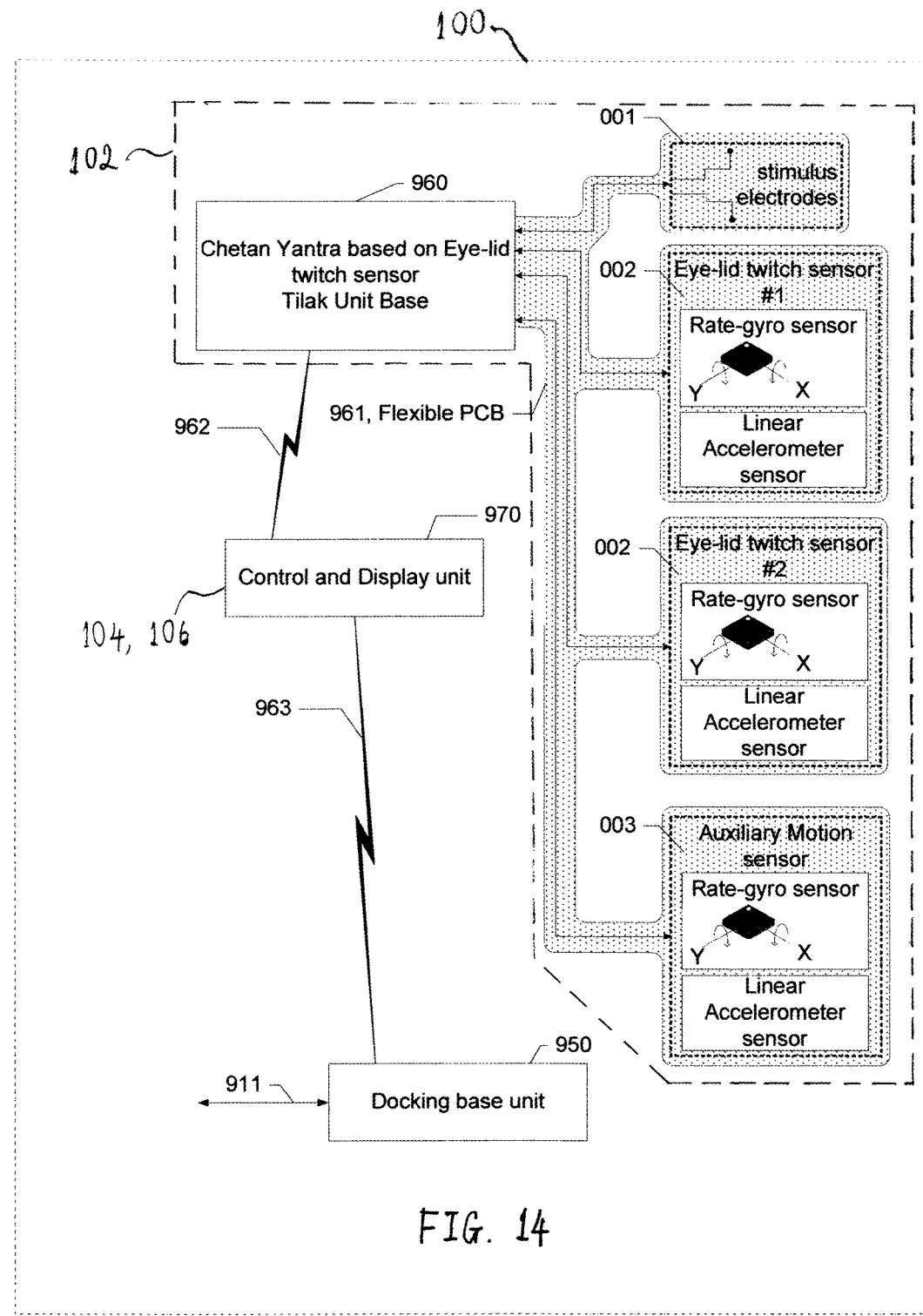
FIGS. 14, 15, 16, and 17 show different embodiments in which the sensing system is targeted at the eye-lid of a patient.

Referring to FIG. 14, the system 100 includes sensing system 102, paralysis assessment system 104, and I/O device 106. The system 100 further includes a Docking base unit 950.

The sensing system 102 includes a fore-head mounted Eye-lid stimulus and twitch sensor 960. The unit 960 includes stimulus electrodes 001, eye-lid twitch sensors 002, and an auxiliary motion sensor 003. The eyelid twitch sensor 002 and Auxiliary sensor 003 can include multi-axis sensor (s) chosen from group of rate-gyro and linear accelerometer.

The system 100 in FIG. 14 also includes a Flexible printed circuit (FPC) 961. The FPC 961 can provide wiring connections as well a substrate onto which components of Stimulus electrode 001, Eye-lid twitch sensors 002, and the Auxiliary sensor 003 are mounted.

Figure 15:
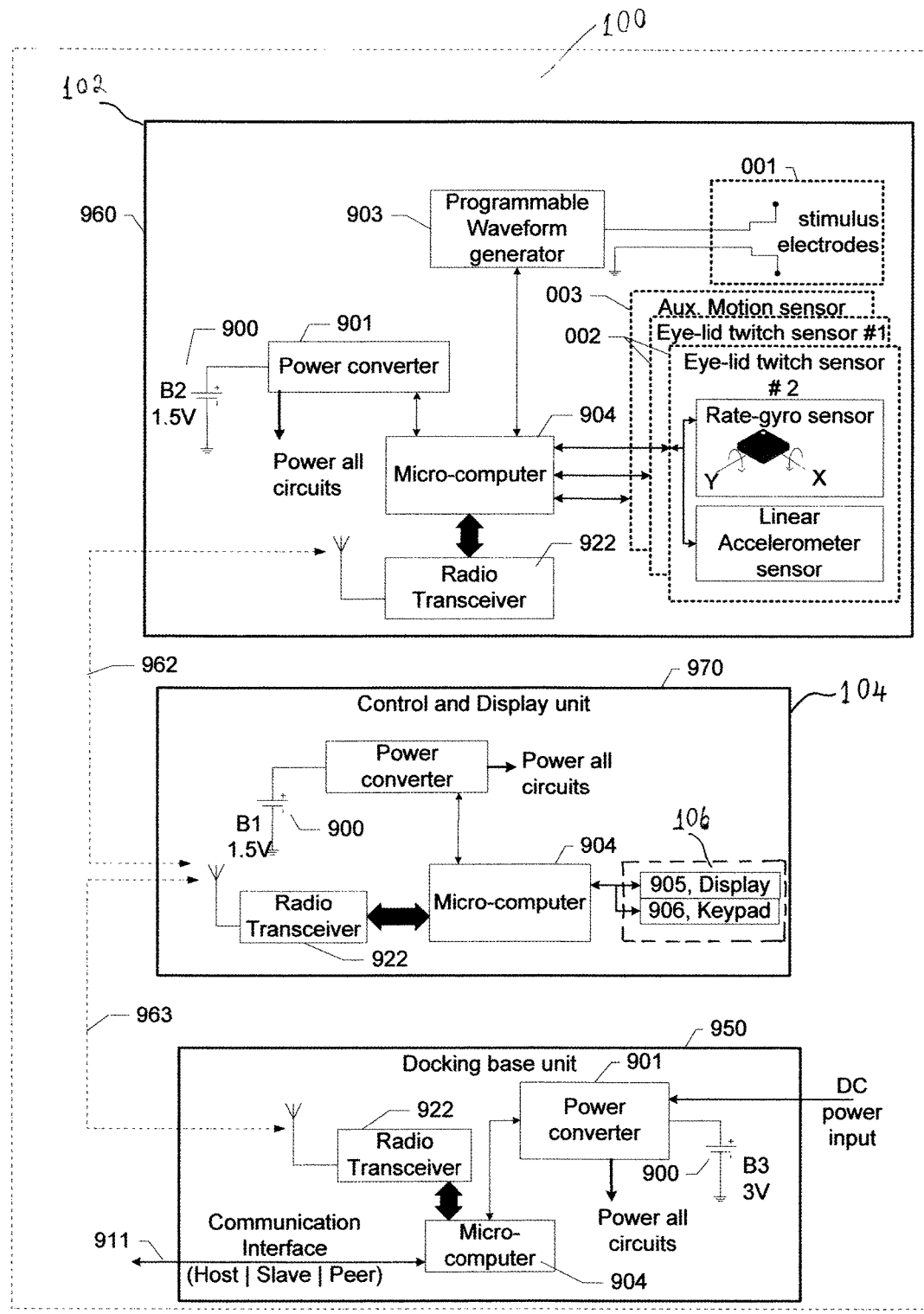

FIG. 15 is a block diagram of the different components within the fore-head mounted Eye-lid stimulus and twitch sensor 960, Control and Display unit 970, and Docking base unit 950.

Referring to FIG. 15, the Fore-head mounted Eye-lid stimulus and twitch sensor 960 includes a Programmable waveform generator 903, Micro-computer 904 (a computer that runs software to implement necessary, communication, sequences the stimulus, sensor measurement, and executes operative control), Power converter 901, Battery 900, Radio-transceiver 922, Stimulus electrodes 001, Eye-lid sensors 002, Auxiliary sensor 003, and Flexible printed circuit (FPC) 961.

The paralysis assessment system 104 includes Control and Display unit 970. The Control and display unit 970 of FIG. 14 is similar to the Control and display unit 940 of FIG. 10, except that the Control and display unit 970 does not have a Programmable waveform generator 903.

Figure 16:
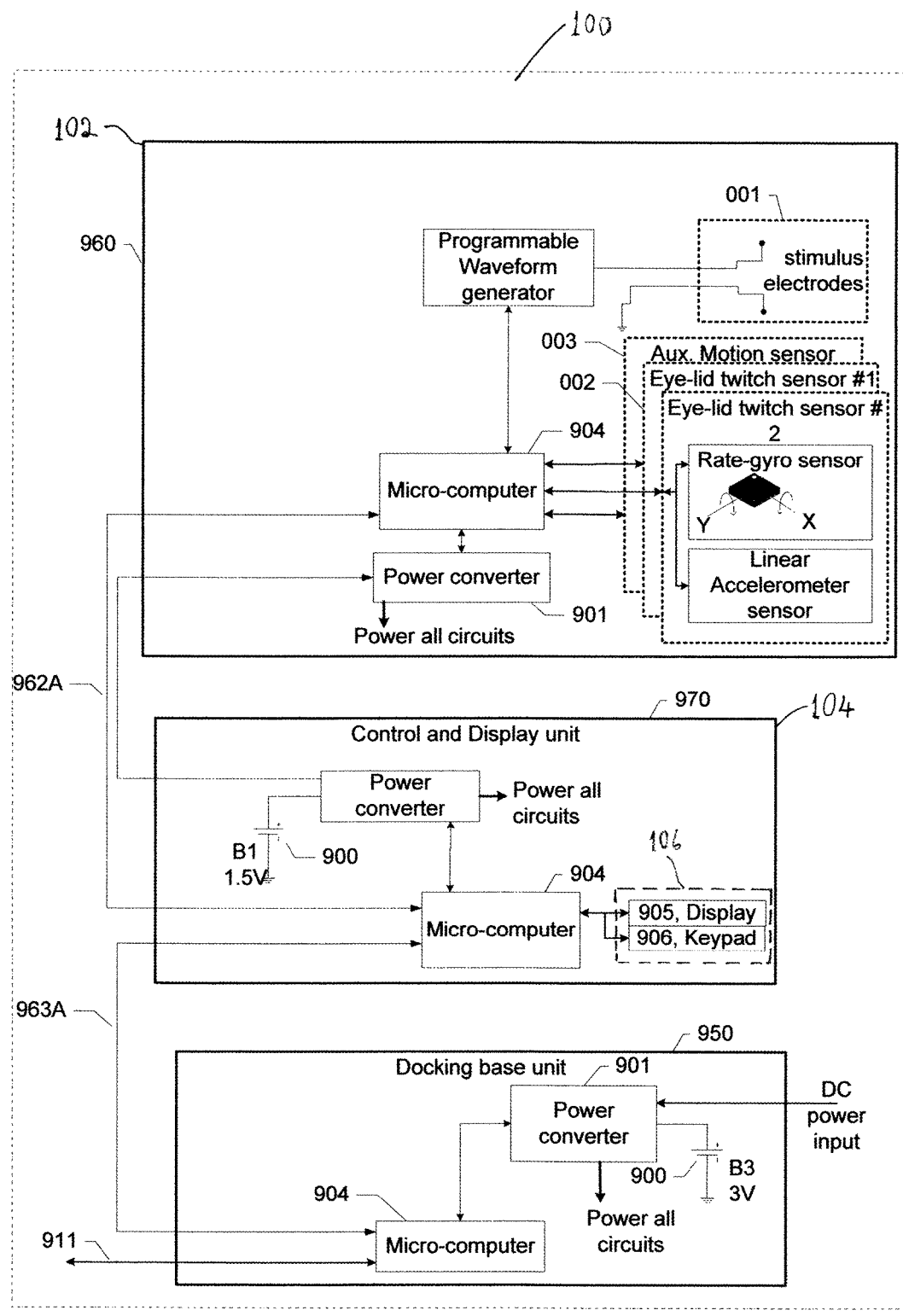
Figure 17:
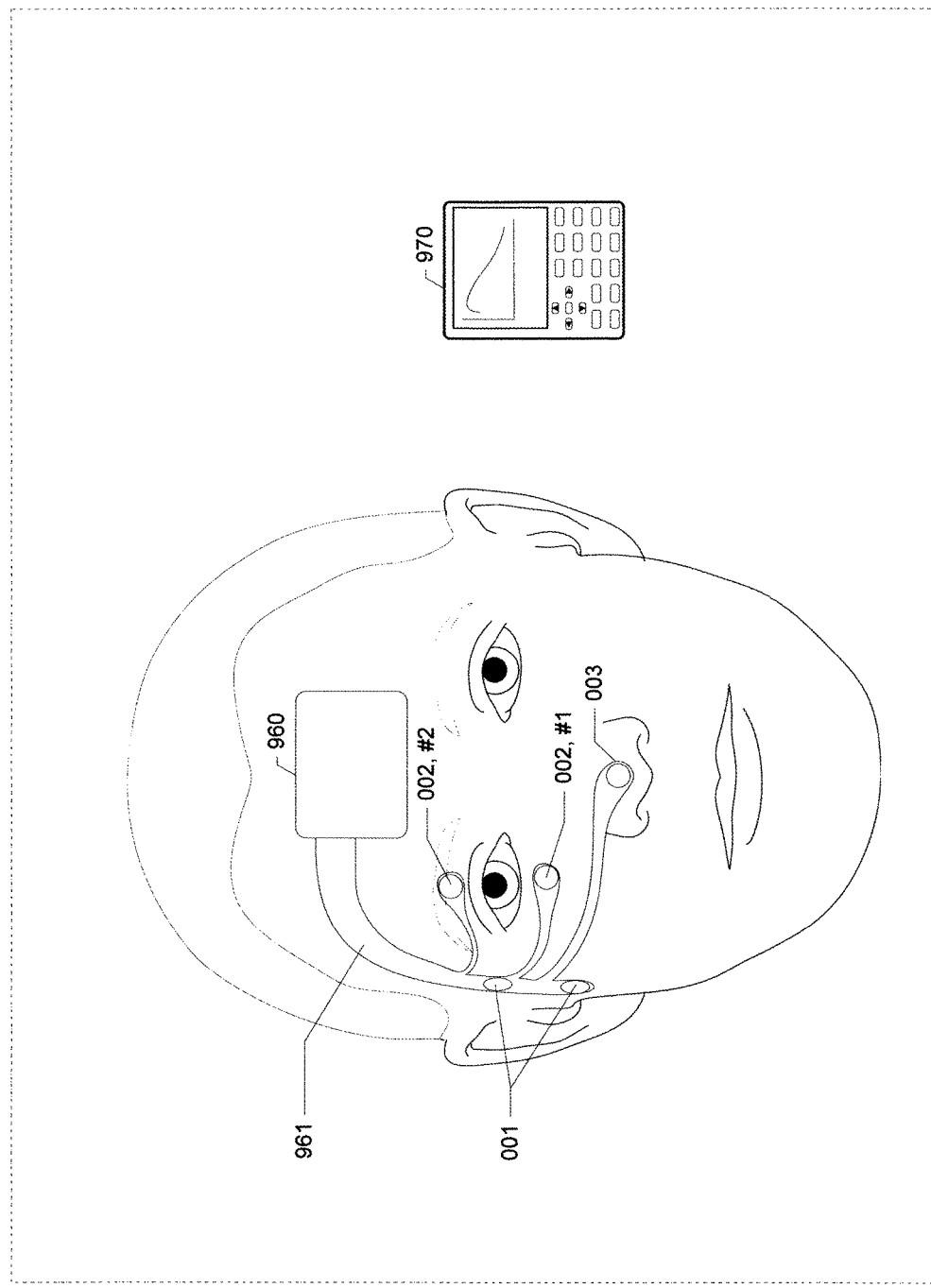

FIG. 17 illustrates how the unit 960 of FIGS. 14-16 can be used on the forehead of a person.

Referring to FIG. 17, the eye-lid twitch sensor (e.g. motion sensor 002) can be mounted near the eye on the fore-head (position #2) or on an area below the eye-lid (position #1). The unit 960 can also be packaged to communicate with Micro-computer 904 via wired connection (FIG. 16) or wireless connection (FIG. 15). Although linear accelerometers are typically adequate in most cases, the use of both rate-gyro sensors and linear accelerometers can provide a robust measure of the muscular response of the Orbicularis Oculi muscle. (See FIG. 13 for the location of the Orbicularis Oculi muscle). As such, more than one type of sensors may be used at the same time to reduce noise and improve robustness. In some embodiments, more than one set of sensors may be used for more accurately capturing the twitch response of Orbicularis Oculi muscle. As shown in FIG. 17, an auxiliary motion sensor 003 can be used if the environment contains a high level of ambient noise vibration.

Referring to FIG. 17, the Flexible printed circuit 961 can provide stimulus connectivity to stimulus electrodes 001. The Flexible printed circuit 961 can also provide a substrate onto which the sensors 002 and 003 can be mounted.

The sensors 002 and 003 are mounted with temporary adhesive on applicable skin surface. In an example, two Sensors 002 are used. One is mounted below the eye brow and other below the eye, corresponding to "Orbicularis Oculi" muscles that move in response to stimulation of Temporal & Zygomatic branches of the 'Facial Nerve'. It is also possible to use just one of these sensors. Compliant and flexible connection allows sensors to easily move and faithfully sense movement.

For greater robustness to ambient vibration, one can employ sensor 003 and locate it on nearby body part (e.g. nose cartilage) that is insensitive to nerve stimulation.

The wired version of unit 960 in FIG. 16 is similar to the wireless version of unit 960 in FIG. 15. As shown in FIG. 16, wired communication links 962A are used to connect unit 960 to the control and display unit 970, and wired communication links 963A are used to connect the control and display unit 970 to the docking base unit 950. In FIG. 15, radio transceivers 922 are used to transmit data between the unit 960, control and display unit 970, and docking base unit 950. It is noted that a wired unit 960 in FIG. 16 may not require a separate battery or power converter, unlike the wireless unit 960 in FIG. 15.

Figure 19:
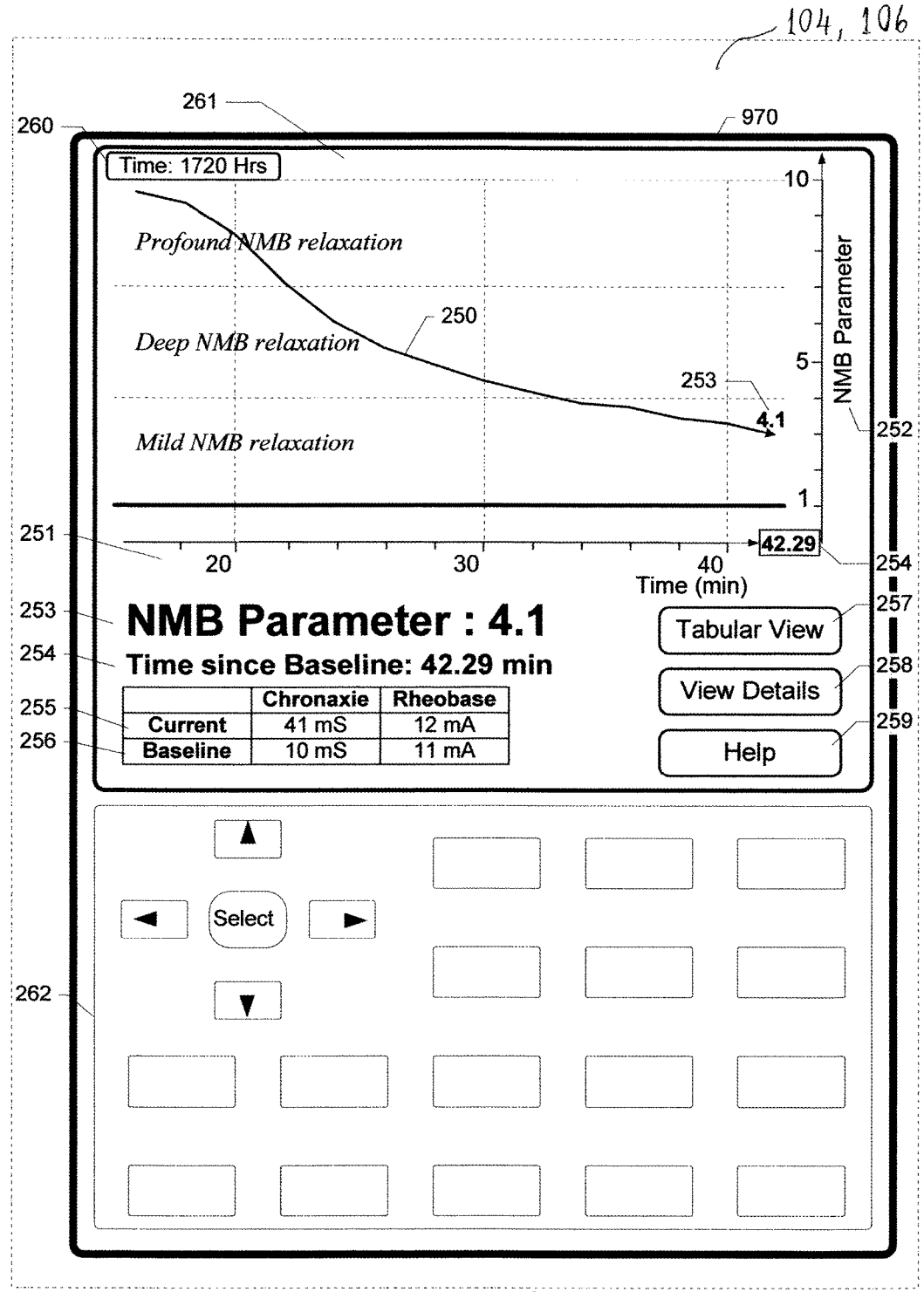
FIG. 19 illustrates an embodiment of a Control and Display unit 970.

FIG. 19 illustrates am embodiment of the Control and Display unit 970.

As shown in FIG. 19, the Control and Display unit 970 provides a graphical user interface. The unit 970 includes information display surface 261 capable of displaying a variety of information based on a user's selection.

The unit 970 includes Home page displays. The Home page displays can include a Graph section and a Dash board section.

The Graph section can display the Trend graph 250 of "NMB Parameter" (or "Mathur parameter", and also the Current NMB Parameter (or Mathur Parameter) 253. In the Graph section, the X-Axis displays progression of time 251 since baseline, and the end of the current elapsed time since baseline 254. The Y-Axis displays a scale of the NMB Parameter 252. The current clock time is also shown (260).

The Dash board section displays the Current NMB Parameter (or Mathur Parameter) 253 and the elapsed time since baseline 254. The Dash board section also displays the current Chronaxie and the Rheobase 255, and the Baseline Chronaxie and Rheobase 256.

The Navigation Option allows users to navigate to other pages. For example, a user can choose to navigate to the "Tabular View" 257, "View Details" 258, or "Help" 259.

The Keypad 262 allows user to provide input. The keypad 262 can include, for example, a membrane keypad, touch pad, or a touch screen overlaid on a display surface.

FIGS. 20, 21, 22, 23, 24, 25, 26, 27, 28 and 29 are flow charts illustrating exemplary methods and sub-processes according to different embodiments of the invention.

The flow charts are described as process or sub-process of workflow with input and return process variables, and therefore relate to programming language constructs.

Figure 28:
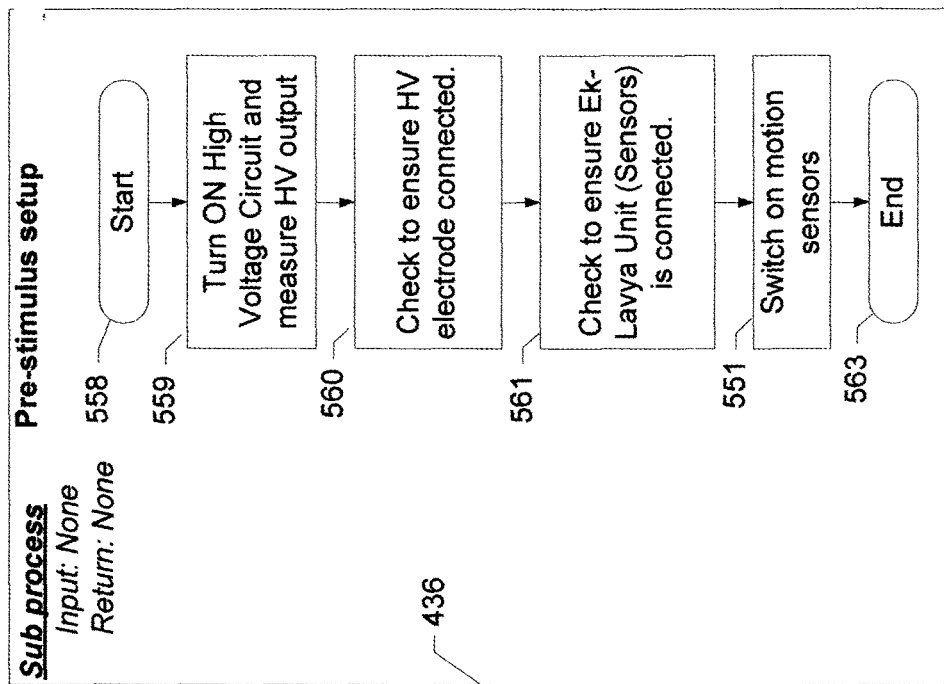

FIG. 28 is a flow chart for the sub-process "Pre-stimulus setup" 436. There are no input or return arguments in the sub-process 436. The sub-process 436 is used to prepare electronic function blocks required for stimulus application.

Referring to FIG. 28, the paralysis assessment system 104 receives a signal that turns on programmable waveform generator 903 (Step 559). The programmable waveform generator 903 measures and verifies that the high-voltage power converter's 902 output voltage is normal (Step 559). Next, the paralysis assessment system 104 performs a basic electrode connectivity check (Step 560), by using 917 to apply a tiny stimulus current (e.g. 0.5 mA) for a very short time, and measuring the resulting current. The resulting current can be measured when the electrodes are properly connected. During Step 561, the paralysis assessment system 104 also checks electrical connectivity with the twitch sensor 002 to ensure the sensors are connected. After confirming that the HV electrodes are connected (Step 560) and that the sensors are connected (Step 561), the paralysis assessment system 104 turns on the twitch sensor (Step 551).

Figure 29:
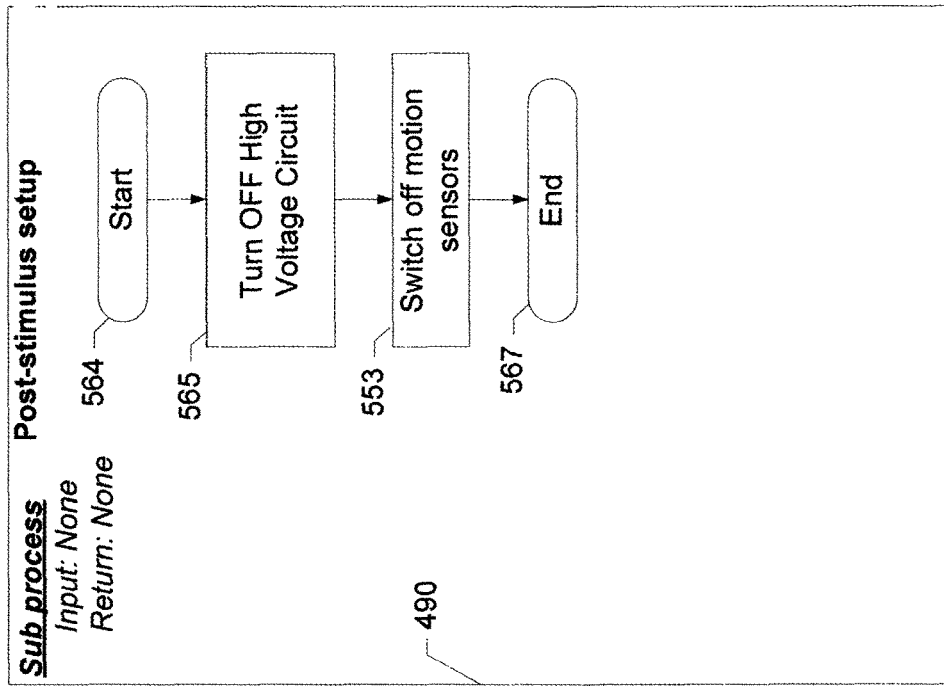

FIG. 29 is a flow chart for the sub-process "Post-stimulus setup" 490. There are no input or return arguments in the sub-process 490. The sub-process 490 is used to shutdown electronic function blocks required for stimulus application when they are not required in the short term, so as to conserve electric energy. Referring to FIG. 29, the paralysis assessment system 104 powers off the programmable waveform generator 903 (Step 565) and then powers off the twitch sensor(s) 002 (Step 553).

Figure 27:
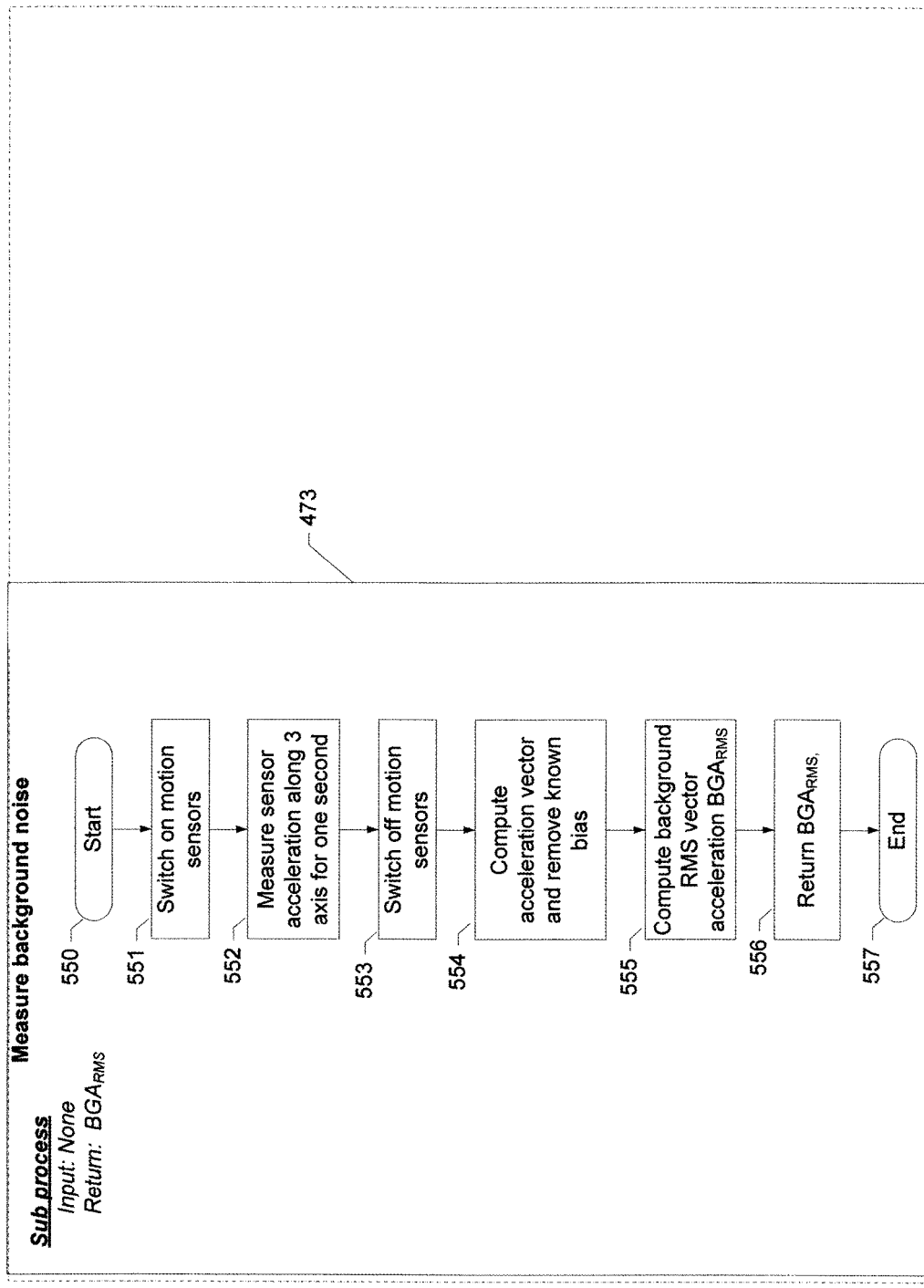

FIG. 27 is a flow chart for the sub-process "Measure background noise" 473. The sub-process 473 measures background noise acceleration 600 reported by the twitch sensors 002 when there is no stimulus applied. There is no input argument. The return argument $BGA_{RMS}$ is the RMS value of the background acceleration vector.

Referring to FIG. 27, the paralysis assessment system 104 first switches on the motion sensors 002 (step 551), and measures the acceleration along the three axes for a second (step 552). As described earlier, in some particular embodiments, fewer axis motion sensors can suffice. The sensors are then powered off (step 553). Based on the collected sensor data, the paralysis assessment system 104 computes the acceleration vector, taking into consideration any bias due to electronics or physical environment (step 554). Next, the paralysis assessment system 104 computes the background root mean square (RMS) value of the acceleration vector for the one second duration ($BGA_{RMS}$) (step 555), and returns the value of $BGA_{RMS}$ (step 556).

Figure 26:
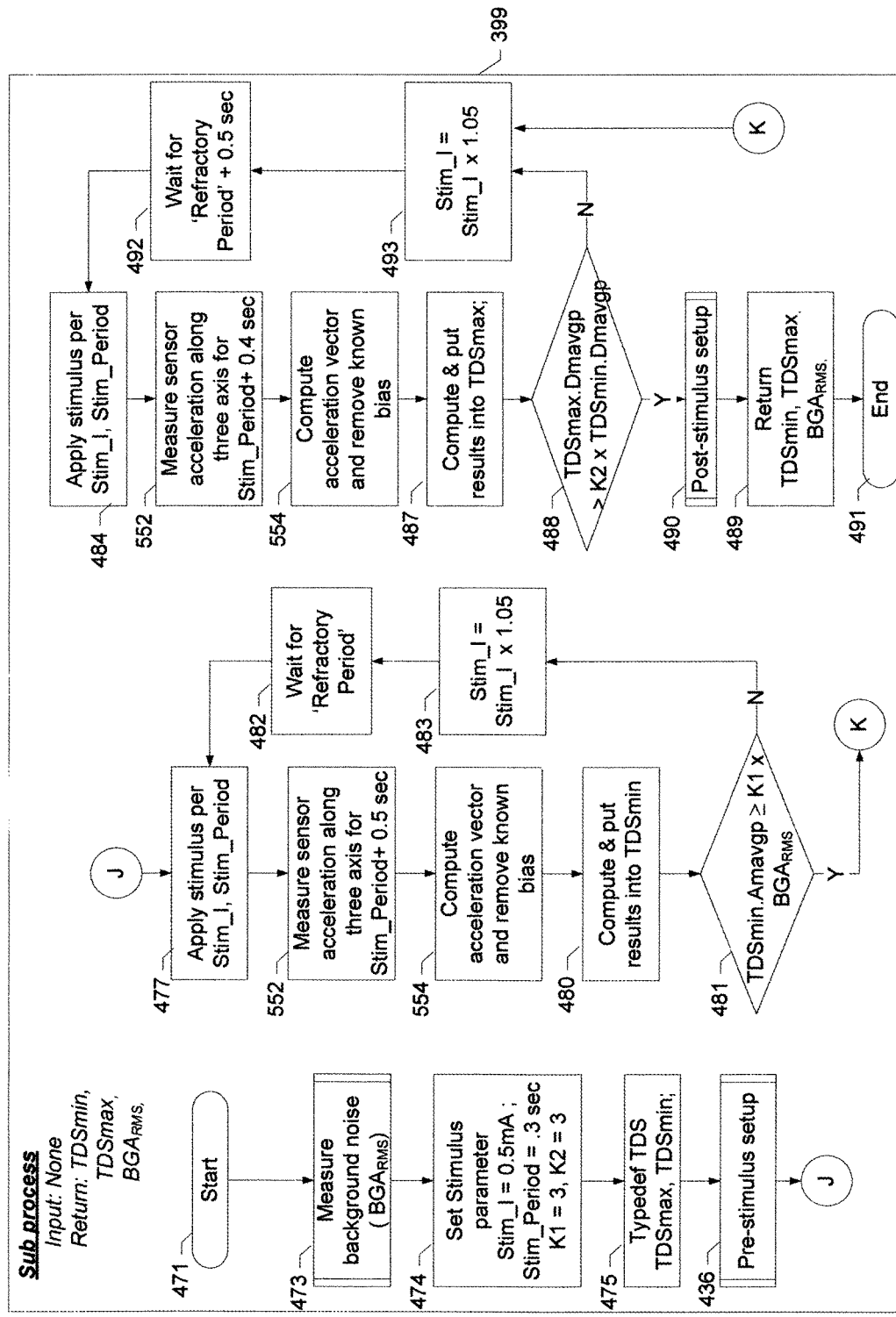

FIG. 26 is a flow chart for the sub-process "Measure background noise, twitch baseline and range" 399. The sub-process 399 measures background noise when there is no stimulus applied, and establishes the baseline twitch movement (that will be used as threshold for all future measurements) and range of physical movement of the sensor (to ensure the target muscle is un-obstructed and free to move over a large range). There is no input argument. The output arguments of the sub-process 399 are $TDS_{min}$, $TDS_{max}$ and $BGA_{RMS}$ (as defined earlier). $TDS_{min}$ is the TDS information corresponding to twitch baseline that is at least K1 (which is a user defined configuration constant) multiplied by the noise threshold ($BGA_{RMS}$). $TDS_{max}$ is the TDS information corresponding to twitch baseline that is at least K2 (which is a user defined configuration constant) multiplied by the $TDS_{min}$ noise threshold ($BGA_{RMS}$). $BGA_{RMS}$ is the RMS value of the background acceleration vector.

Referring to FIG. 26, when the paralysis assessment system 104 is executing the sub-process 399, the paralysis assessment system 104 first measures the background noise by invoking the sub-process "Measure background noise" 473 to return $BGA_{RMS}$. (See FIG. 27). Next, the paralysis assessment system 104 initializes the stimulus parameters (local variables) (step 474). The stimulus parameters include Stim_I, Stim_Period, K1, and K2. Stim_I is the stimulation current that will be used in future iterations. Stim_Period is the time period the stimulation will be applied. K1 is a user defined configuration constant that sets minimum signal to noise ratio that is suitable to ensure reliable twitch sensing. K2 is a user defined configuration constant that ensures there is enough physical space to sense physiological movement thus ensuring there is no physical obstruction preventing movement.

In some embodiments, Stim_I is initially set to 0.5 mA, Stim_Period is set to 0.3 second, the range of K1 is generally 100>K1>3, and the range of K2 is generally 20>K2>2.

Referring to FIG. 26, the paralysis assessment system 104 then instantiates the TDS type data structures $TDS_{min}$ and $TDS_{max}$ (step 475). Next, the sub-process "Pre-stimulus setup" 436 is invoked.

As previously described in FIG. 28, the motion sensors are switched on (step 551) after the sub-process "Pre-stimulus setup" 436 is completed. Next, referring to FIG. 26, the paralysis assessment system 104 applies a Stimulus of 'Stim_I' to the patient's muscle for a duration of 'Stim_Period' (step 477). Next, the paralysis assessment system 104 measures the physiological response from data generated by the motion sensors 002 (acceleration sensors, although other sensors can be similarly used) along the three axes over the duration of the stimulus (with additional 0.5 seconds) (step 552), at a suitable sampling interval (e.g., 1 mSec). Based on the collected data, the paralysis assessment system 104 computes the acceleration vector, velocity vector, and displacement vector, taking into consideration any bias due to electronics or physical environment (step 554). Next, the paralysis assessment system 104 extracts the twitch parameters and populate the results in $TDS_{min}$ (step 480).

Next, in sub-process 399 of FIG. 26, the paralysis assessment system 104 checks if the physiological response (TDSmin.Amavgp) to the stimulus is at least K1 multiplied by the RMS background noise ($BGA_{RMS}$) and a minimum twitch distance ('MinTwitchDisplacement') (Step 481). If TDSmin.Amavgp is less than $K1 \times BGA_{RMS}$, the Stimulation current (Stim_I) is incremented a small fraction (e.g., 5%) (step 483). After a refractory period has passed (to allow the neuromuscular system to recover back from the previous stimulus) (step 482), the paralysis assessment system 104 again iterates step 477 through step 481 until TDSmin.Amavgp is more than or equal to $K1 \times BGA_{RMS}$. In some embodiments, the paralysis assessment system 104 can use other search algorithms (e.g., binary search), instead of the linear search iterative loop in the example of FIG. 26.

Next, the paralysis assessment system 104 verifies if there is enough physical space to sense physiological movement, to ensure there is no physical obstruction preventing movement.

Referring to step 493 of FIG. 26, the Stimulation current (Stim_I) is incremented a small fraction (e.g., 5%). The value of 'Stim_I' in step 493 corresponds to the case in which TDSmin.Amavgp is more than or equal to $K1 \times BGA_{RMS}$ (from step 481). After a refractory period (with additional 0.5 seconds) has passed (to allow the neuromuscular system to recover back from the previous stimulus) (step 492), the paralysis assessment system 104 applies a Stimulus of 'Stim_I' to the patient's muscle for a duration of 'Stim_Period' (step 484). Next, the paralysis assessment system 104 measures the physiological response from data generated by the motion sensors 002 (acceleration sensors, although other sensors can be similarly used) along the three axes over the duration of the stimulus (with additional 0.4 seconds) (step 552), at a suitable sampling interval (e.g., 1 mSec). Based on the collected data, the paralysis assessment system 104 computes the acceleration vector, velocity vector, and displacement vector, taking into consideration any bias due to electronics or physical environment (step 554). Next, the paralysis assessment system 104 extracts the twitch parameters and populates the results in $TDS_{max}$ (step 487).

Next, the paralysis assessment system 104 checks if the physiological displacement response (TDSmax.Dmavgp) to the stimulus is at least K2 multiplied by the baseline physiological displacement response ($TDS_{min}$.Dmavgp), or if Stim_I≥Stim_I_limit, where Stim_I_limit is the maximum permissible stimulus current (Step 488). If TDSmax.Dmavgp is less than $K2 \times TDS_{min}$.Dmavgp, (or Stim_I is less than Stim_I_limit), the Stimulation current (Stim_I) is incremented a small fraction (e.g., 5%) (step 493). After another refractory period (with additional 0.5 seconds) has passed (to allow the neuromuscular system to recover back from the previous stimulus) (step 492), the paralysis assessment system 104 again iterates step 484 through step 488 until TDSmax.Dmavgp is more than $K2 \times TDS_{min}$.Dmavgp (or Stim_I is more than or equal to Stim_I_limit). In some embodiments, the paralysis assessment system 104 can use other search algorithms (e.g., binary search), instead of the linear search iterative loop in the example of FIG. 26.

To end the sub-process 399, the paralysis assessment system 104 shuts down the stimulus electronics by executing the sub-process 490, and returning $TDS_{min}$, $TDS_{max}$ and $BGA_{RMS}$ to the calling workflow (step 489).

Figure 25:
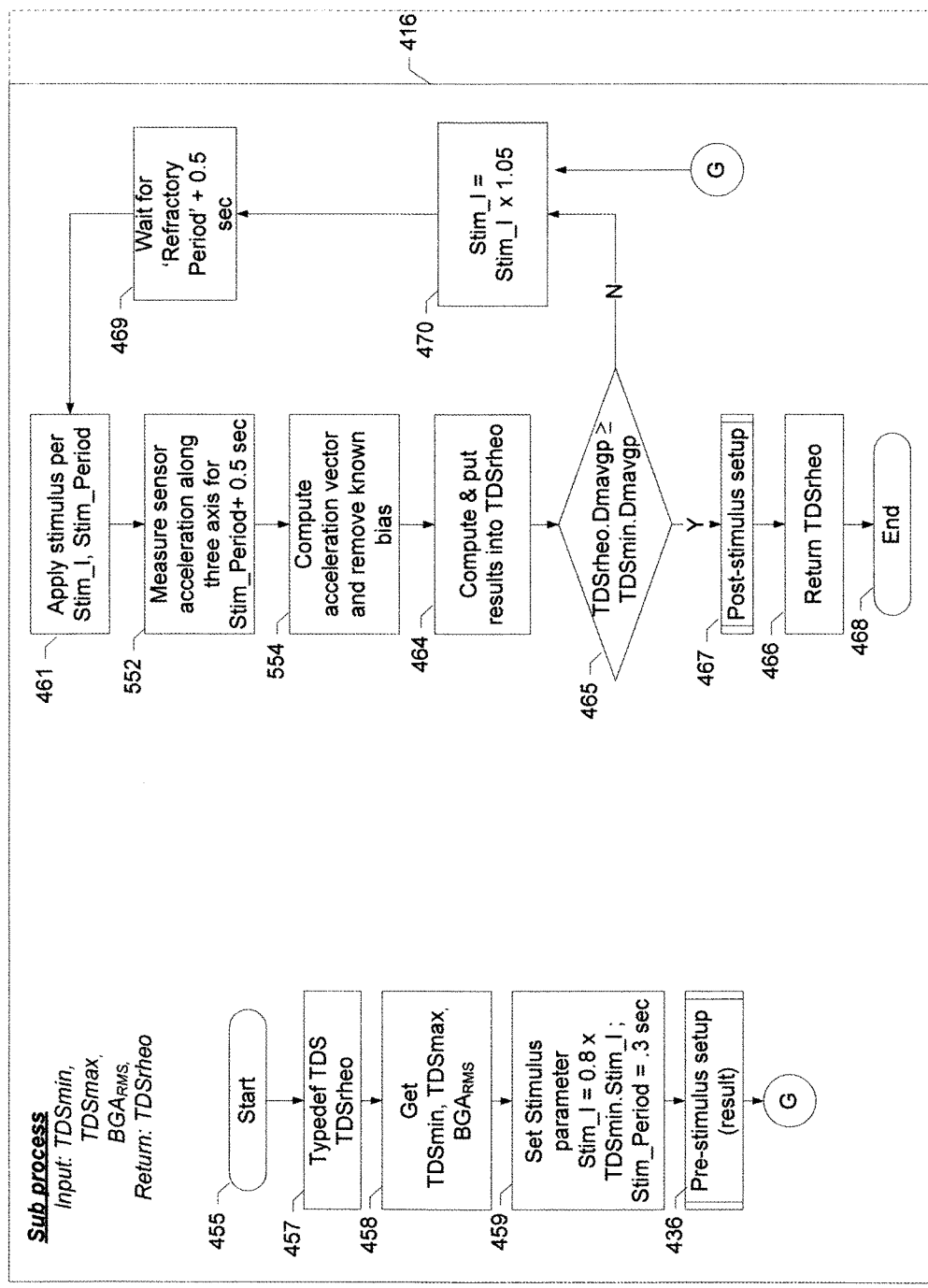

FIG. 25 is a flow chart for the sub-process "Measure Rheobase" 416. The sub-process 416 measures Rheobase. The sub-process 416 requires input arguments $TDS_{min}$, $TDS_{max}$ and $BGA_{RMS}$ obtained from a prior invocation of the sub-process "Measure background noise, twitch baseline and range" 399. The return argument of the sub-process 416 is $TDS_{rheo}$. $TDS_{rheo}$ is the TDS information corresponding to successful measurement of Rheobase.

Referring to FIG. 25, the paralysis assessment system 104 instantiates the TDS type data structures $TDS_{rheo}$ (step 457). The paralysis assessment system 104 then obtains the input arguments (step 458), and initializes the stimulus parameters (local variables) (step 459). Stim_I is the stimulation current that will be used in future iterations, and is initially set to below TDSmin.Stim_I. Stim_Period is set to a large interval.

In some embodiments, Stim_I=0.8×TDSmin.Stim_I, and the Stim_Period is about 0.3 seconds.

With reference to FIG. 25, the sub-process "Pre-stimulus setup" 436 is invoked. As previously described in FIG. 28, the motion sensors are switched on (step 551) after the sub-process "Pre-stimulus setup" 436 is completed.

Referring to step 470 of FIG. 25, the Stimulation current (Stim_I) is incremented a small fraction (e.g., 5%). The value of 'Stim_I' in step 470 corresponds to the value of Stim_I=0.8×TDSmin.Stim_I (from step 459). After a refractory period (with additional 0.5 seconds) has passed (to allow the neuromuscular system to recover back from the previous stimulus) (step 469), the paralysis assessment system 104 applies a Stimulus of 'Stim_I' to the patient's muscle for a duration of 'Stim_Period' (step 461). Next, the paralysis assessment system 104 measures the physiological response from data generated by the motion sensors 002 (acceleration sensors, although other sensors can be similarly used) along the three axes over the duration of the stimulus (with additional 0.5 seconds) (step 552), at a suitable sampling interval (e.g., 1 mSec). Based on the collected data, the paralysis assessment system 104 computes the acceleration vector, velocity vector, and displacement vector, taking into consideration any bias due to electronics or physical environment (step 554). Next, the paralysis assessment system 104 extracts the twitch parameters and populates the results in $TDS_{rheo}$ (step 464).

Next, the paralysis assessment system 104 checks if the physiological displacement response ($TDS_{rheo}$.Dmavgp) to the stimulus is at least equal to the baseline physiological displacement response ($TDS_{min}$.Dmavgp) (step 465).

If $TDS_{rheo}$.Dmavgp is less than $TDS_{min}$.Dmavgp, the Stimulation current (Stim_I) is incremented a small fraction (e.g., 5%) (step 470). After another refractory period (with additional 0.5 seconds) has passed (to allow the neuromuscular system to recover back from the previous stimulus) (step 469), the paralysis assessment system 104 again iterates step 461 through step 465 until $TDS_{rheo}$.Dmavgp is at least equal to $TDS_{min}$.Dmavgp. In some embodiments, the paralysis assessment system 104 can use other search algorithms (e.g., binary search), instead of the linear search iterative loop in the example of FIG. 26.

To end the sub-process 416, the paralysis assessment system 104 shuts down the stimulus electronics by executing the sub-process 'Post-stimulus setup' 467, and returning $TDS_{rheo}$ to the calling workflow (step 466).

Figure 24:
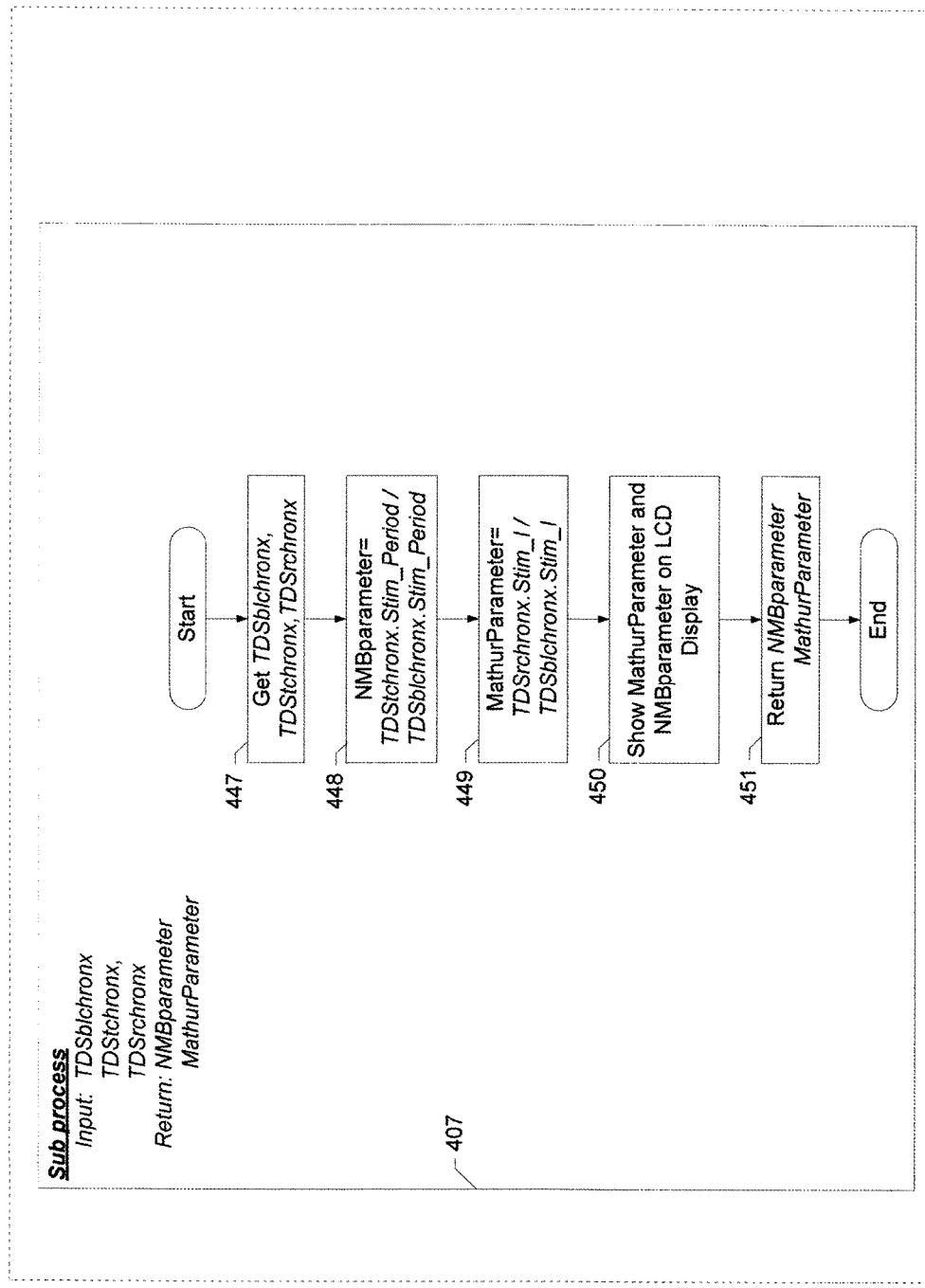

FIG. 24 is a flow chart for the sub-process "Compute and display NMB Parameter and Mathur Parameter" 407. The sub-process 407 requires input arguments $TDS_{blchronx}$, $TDS_{tchronx}$ and $TDS_{rchronx}$. The return arguments are NMB parameter and Mathur Parameter corresponding to the current "NMB Parameter" and "Mathur Parameter", respectively.

During sub-process 407, the paralysis assessment system 104 first obtains the input arguments (step 447), and then computes the NMB Parameter and Mathur Parameter based on the input attributes.

NMB Parameter=$TDS_{tchronx}$.Stim_Period/$TDS_{blchronx}$.Stim_Period (step 448)

MathurParameter=$TDS_{rchronx}$.Stim_I/$TDS_{blchronx}$.Stim_I (step 449)

Next, the paralysis assessment system 104 displays the updated NMB and Mathur parameters on the 'Control and display unit' 905, and returns the NMB parameter and Mathur Parameter to the calling workflow (step 451).

Figure 23:
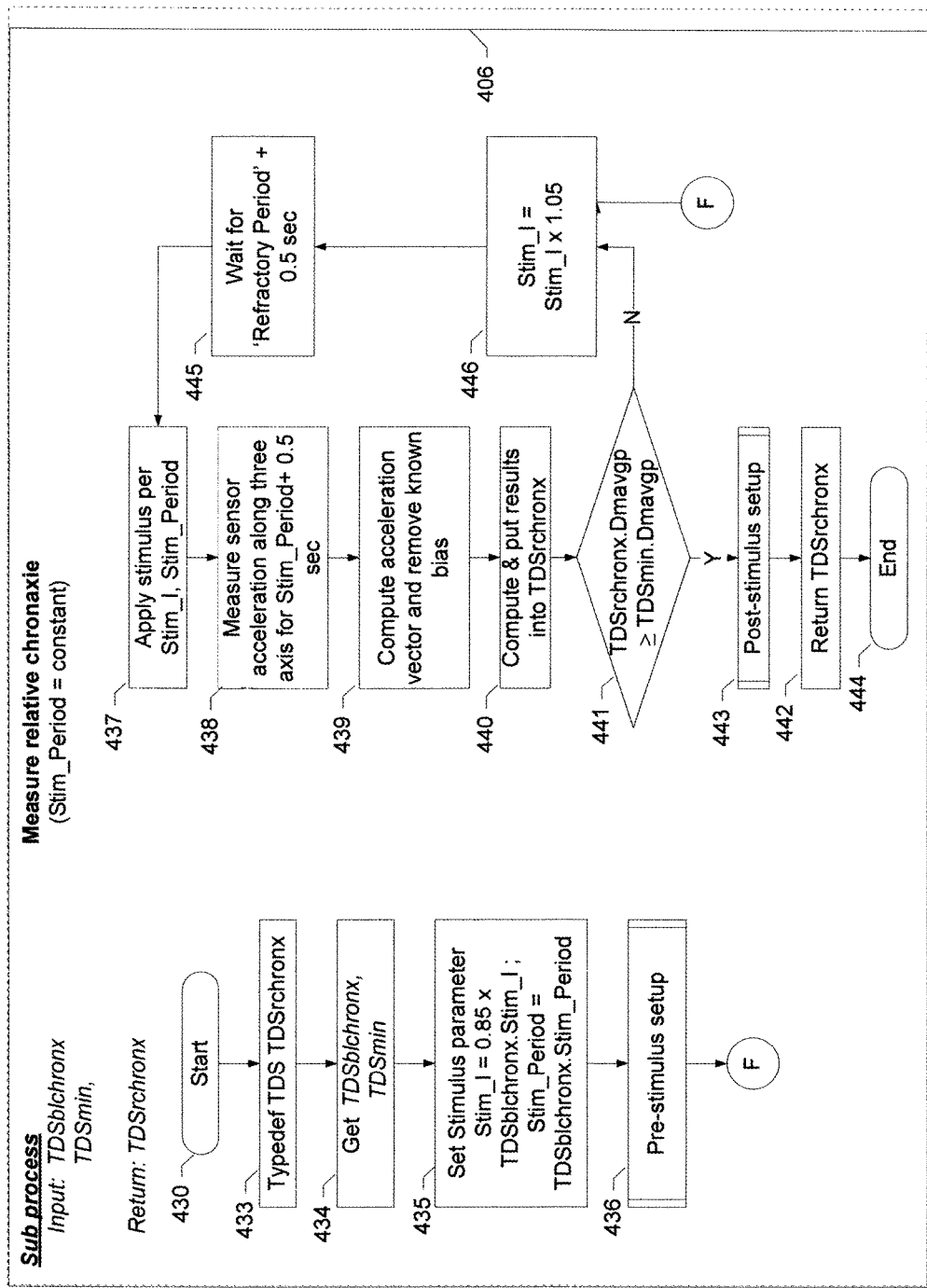

FIG. 23 is a flow chart for the sub-process "Measure relative chronaxie" 406. The sub-process 406 measures relative chronaxie (the basis for the Mathur Parameter) by setting the Stim_Period equal to the baseline chronaxie, and changing the Stim_I. The sub-process 406 requires input arguments $TDS_{blchronax}$ and $TDS_{min}$, and returns the argument $TDS_{rchronx}$.

Referring to FIG. 23, the paralysis assessment system 104 first instantiates the TDS type data structures $TDS_{rchronx}$ (step 433). The paralysis assessment system 104 then obtains the input arguments (step 434), and sets the initial value to stimulus parameters (local variables) (step 435). Stim_I is the stimulation current that will be used in future iterations, and is initially set close to TDSblchronx.Stim_I.

In some embodiments, Stim_I=0.85×TDSblchronx.Stim_I, and the Stim_Period is set to Stim_Period=TDSblchronx.Stim_Period.

Referring again to FIG. 23, the sub-process "Pre-stimulus setup" 436 is invoked. As previously described in FIG. 28, the motion sensors are switched on (step 551) after the sub-process "Pre-stimulus setup" 436 is completed.

Referring to step 446 of FIG. 23, the Stimulation current (Stim_I) is incremented a small fraction (e.g., 5%). The value of 'Stim_I' in step 446 corresponds to the the value of Stim_I=0.85×TDSblchronx.Stim_I (from step 435). After a refractory period (with additional 0.5 seconds) has passed (to allow the neuromuscular system to recover back from the previous stimulus) (step 445), the paralysis assessment system 104 applies a Stimulus of 'Stim_I' to the patient's muscle for a duration of 'Stim_Period' (step 437). Next, the paralysis assessment system 104 measures the physiological response from data generated by the motion sensors 002 (acceleration sensors, although other sensors can be similarly used) along the three axes over the duration of the stimulus (with additional 0.5 seconds) (step 438), at a suitable sampling interval (e.g., 1 mSec). Based on the collected data, the paralysis assessment system 104 computes the acceleration vector, velocity vector, and displacement vector, taking into consideration any bias due to electronics or physical environment (step 439). Next, the paralysis assessment system 104 extracts the twitch parameters and populates the results in $TDS_{rchronx}$ (step 440).

Next, the paralysis assessment system 104 checks if the physiological displacement response ($TDS_{rchronx}$.Dmavgp) to the stimulus is at least equal to the baseline physiological displacement response ($TDS_{min}$.Dmavgp) (step 441).

If $TDS_{rchronx}$.Dmavgp is less than $TDS_{min}$.Dmavgp, the Stimulation current (Stim_I) is incremented a small fraction (e.g., 5%) (step 446). After another refractory period (with additional 0.5 seconds) has passed (to allow the neuromuscular system to recover back from the previous stimulus) (step 445), the paralysis assessment system 104 again iterates step 437 through step 441 until $TDS_{rchronx}$.Dmavgp is at least equal to $TDS_{min}$.Dmavgp. In some embodiments, the paralysis assessment system 104 can use other search algorithms (e.g., binary search), instead of the linear search iterative loop in the example of FIG. 23.

To end the sub-process 406, the paralysis assessment system 104 shuts down the stimulus electronics by executing the sub-process 'Post-stimulus setup' 443, and returning $TDS_{rchronx}$ to the calling workflow (step 442).

Figure 22:
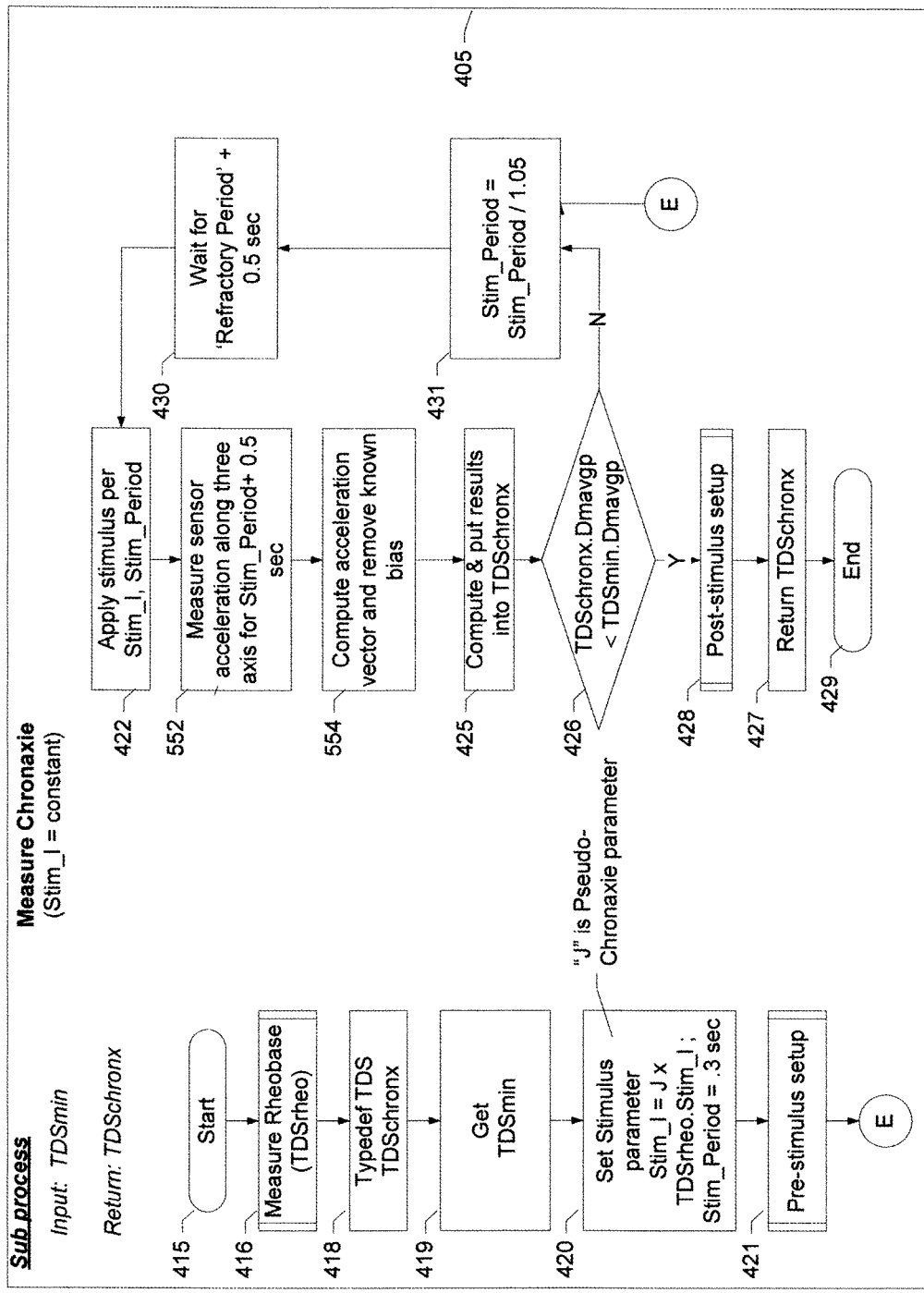

FIG. 22 is a flow chart for the sub-process "Measure Chronaxie" 405. The sub-process 405 measures chronaxie (the basis for NMB Parameter). The sub-process 405 requires the input arguments $TDS_{min}$, and returns the argument $TDS_{chronx}$.

The sub-process 405 first invokes the sub-process "Measure Rheobase" 416 which returns $TDS_{rheo}$. See FIG. 25.

Referring to FIG. 22, the paralysis assessment system 104 instantiates the TDS type data structures $TDS_{chronx}$ (step 418). The paralysis assessment system 104 then obtains the input arguments (step 419), and sets the initial value to the stimulus parameters (local variables) (step 420). Stim_I is set to Stim_I=J×TDSrheo.Stim_I where J is the chosen Pseudo-chronaxie multiplier. Stim_Period is the time period the stimulation will be applied in future iterations, and is initially set to a large interval. In some embodiments, the Stim_Period is typically 0.3 seconds.

With reference to FIG. 22, the sub-process "Pre-stimulus setup" 421 is invoked. As previously described in FIG. 28, the motion sensors are switched on (step 551) after the sub-process "Pre-stimulus setup" 421 is completed.

Referring to step 431 of FIG. 22, the stimulus period 'Stim_Period' is reduced by a small fraction (e.g., 5%). The values of Stim_I and the Stim_Period in step 431 correspond respectively to the values of Stim_I and Stim_Period (e.g., 0.3 seconds) (from step 420). After a refractory period (with additional 0.5 seconds) has passed (to allow the neuromuscular system to recover back from the previous stimulus) (step 430), the paralysis assessment system 104 applies a Stimulus of 'Stim_I' to the patient's muscle for a duration of 'Stim_Period' (step 422). Next, the paralysis assessment system 104 measures the physiological response from data generated by the motion sensors 002 (acceleration sensors, although other sensors can be similarly used) along the three axes over the duration of the stimulus (with additional 0.5 seconds) (step 552), at a suitable sampling interval (e.g., 1 mSec). Based on the collected data, the paralysis assessment system 104 computes the acceleration vector, velocity vector, and displacement vector, taking into consideration any bias due to electronics or physical environment (step 554). Next, the paralysis assessment system 104 extracts the twitch parameters and populates the results in $TDS_{chronx}$ (step 425).

Next, the paralysis assessment system 104 checks if the physiological displacement response ($TDS_{chronx}$.Dmavgp) to the stimulus is less than the baseline physiological displacement response ($TDS_{min}$.Dmavgp) (Step 426).

If $TDS_{chronx}$.Dmavgp is not less than $TDS_{min}$.Dmavgp, the Stimulation period (Stim_Period) is reduced by a small fraction (e.g., 5%) (step 431). After another refractory period (with additional 0.5 seconds) has passed (to allow the neuromuscular system to recover back from the previous stimulus) (step 430), the paralysis assessment system 104 again iterates step 422 through step 426 until $TDS_{chronx}$.Dmavgp is less than $TDS_{min}$.Dmavgp. In some embodiments, the paralysis assessment system 104 can use other search algorithms (e.g., binary search), instead of the linear search iterative loop in the example of FIG. 22.

To end the sub-process 405, the paralysis assessment system 104 shuts down the stimulus electronics by executing the sub-process 'Post-stimulus setup' 428, and returning TDS$_{chronx}$ to the calling workflow (step 427).

Figure 20:
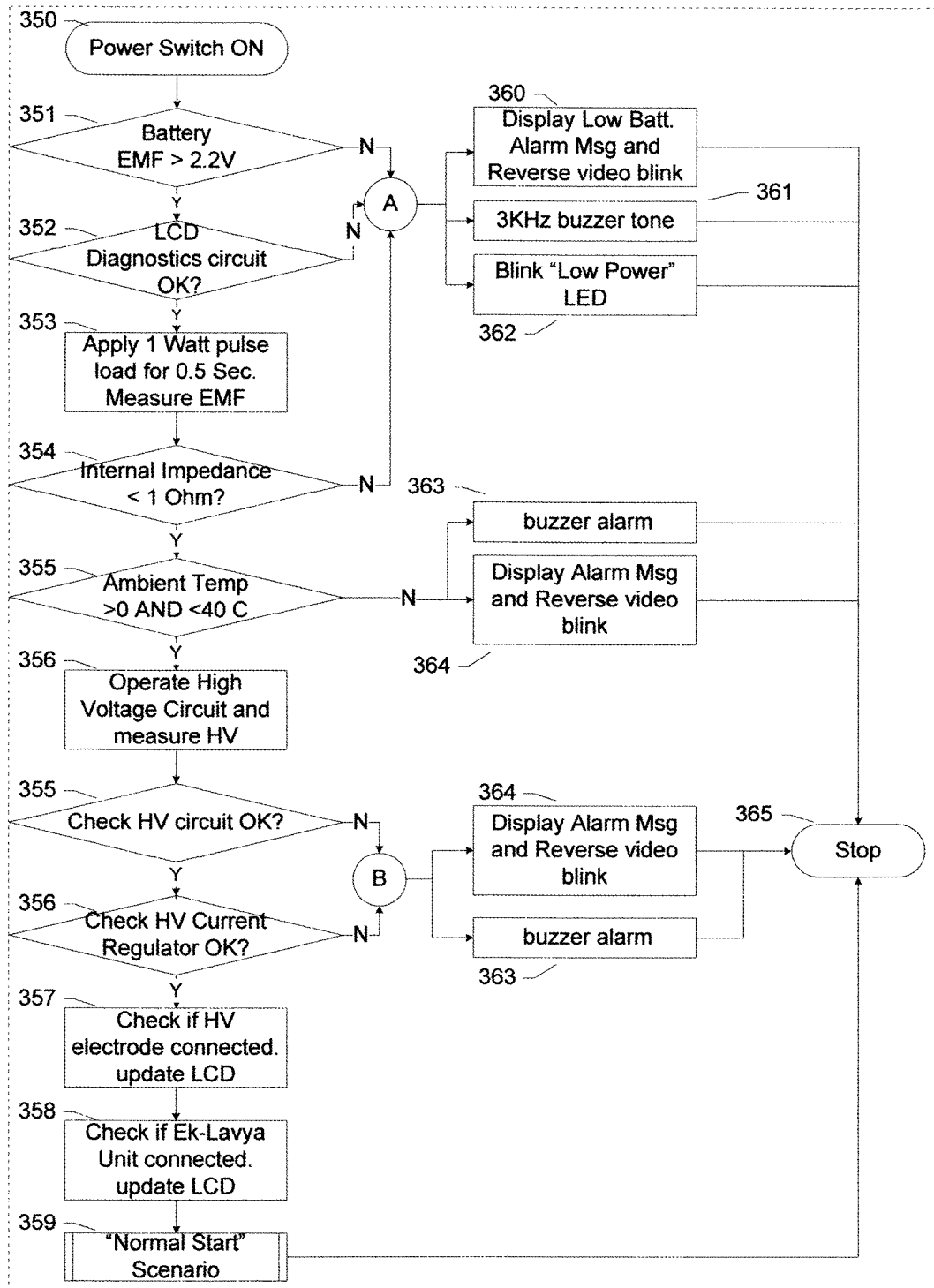

FIG. 20 is a main workflow that starts with "Power Switch ON" 350. The paralysis assessment system 104 performs a series of self-tests including a battery test, a temperature test, a HV test, and a Connectivity check.

In the Battery test, the paralysis assessment system 104 first determines if the battery EMF is in a healthy range (step 351). The paralysis assessment system 104 also checks for the battery's internal impedance, by applying a heavy power load and measuring the incremental change in terminal voltage (step 352). If the battery or LCD diagnostics fail, the paralysis assessment system 104 issues an alarm message on LCD display (step 360), as well as a buzzer tone (step 361) and blink LED for "Low power indication" (step 362).

In the Temperature test, the paralysis assessment system 104 checks the ambient temperature range (step 355), and if the ambient temperature falls outside the designated range, the paralysis assessment system 104 provides a suitable error message on display (step 364) and error buzzer alarm (step 363).

In the HV test, the paralysis assessment system 104 checks the high voltage power converter which is a critical element of the system (step 902). The paralysis assessment system 104 checks for proper operation of the high voltage power converter including the output voltage (step 355). If the high voltage power converter fails to operate properly, the paralysis assessment system 104 issues an error message on the display (step 364) and error buzzer alarm (step 363).

In a Connectivity check, the paralysis assessment system 104 checks for electrical connectivity of the stimulus electrode 001 and the twitch sensor 002, and updates the connectivity status on the display accordingly.

Upon determining that all the checks, the paralysis assessment system 104 starts the workflow sub-process "Normal Start" that operate in an infinite loop (step 359).

Figure 21A:
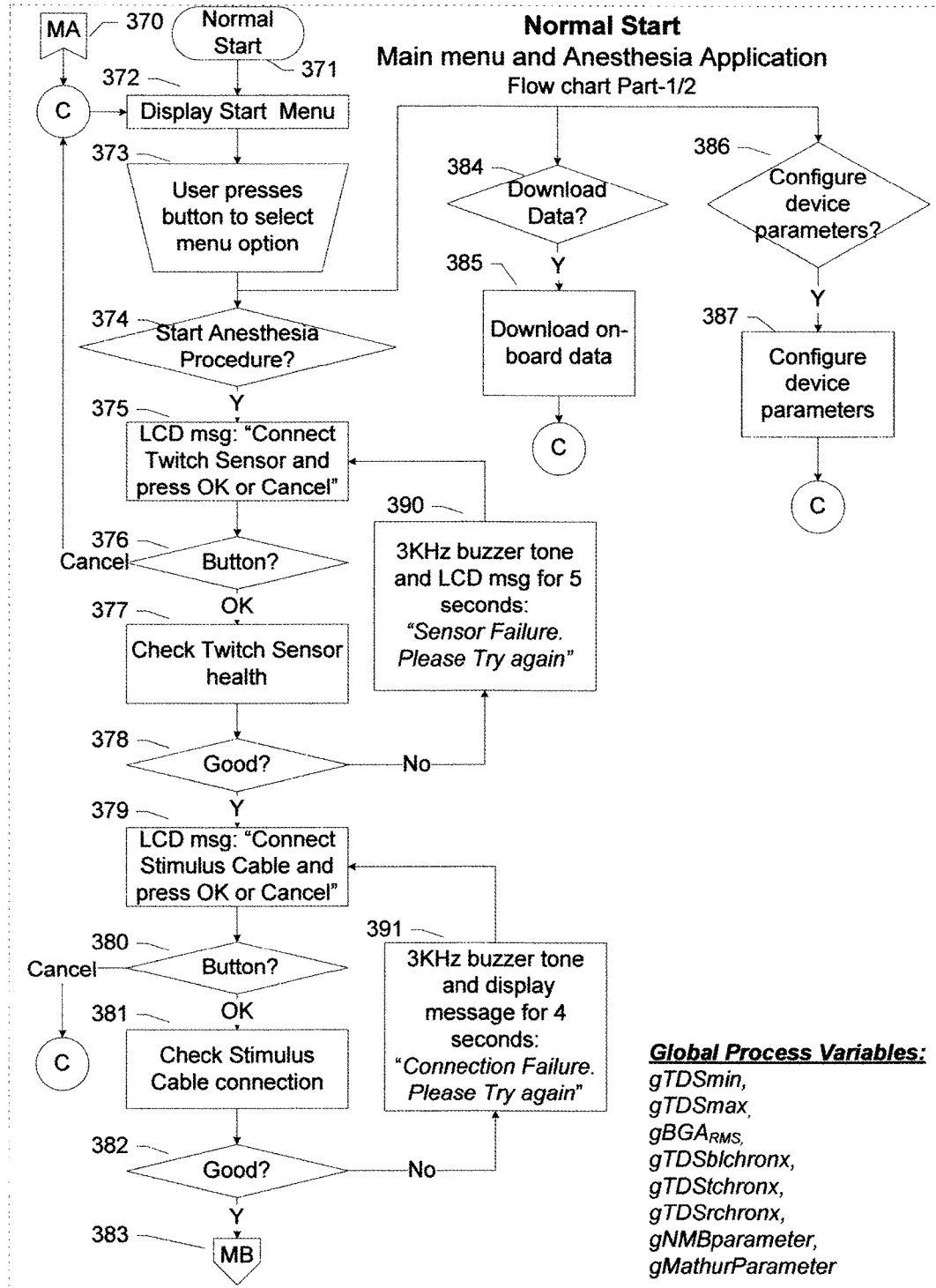
FIGS. 21A and 21B show the principal workflow "Normal Start" operating in infinite loop.
Figure 21B:
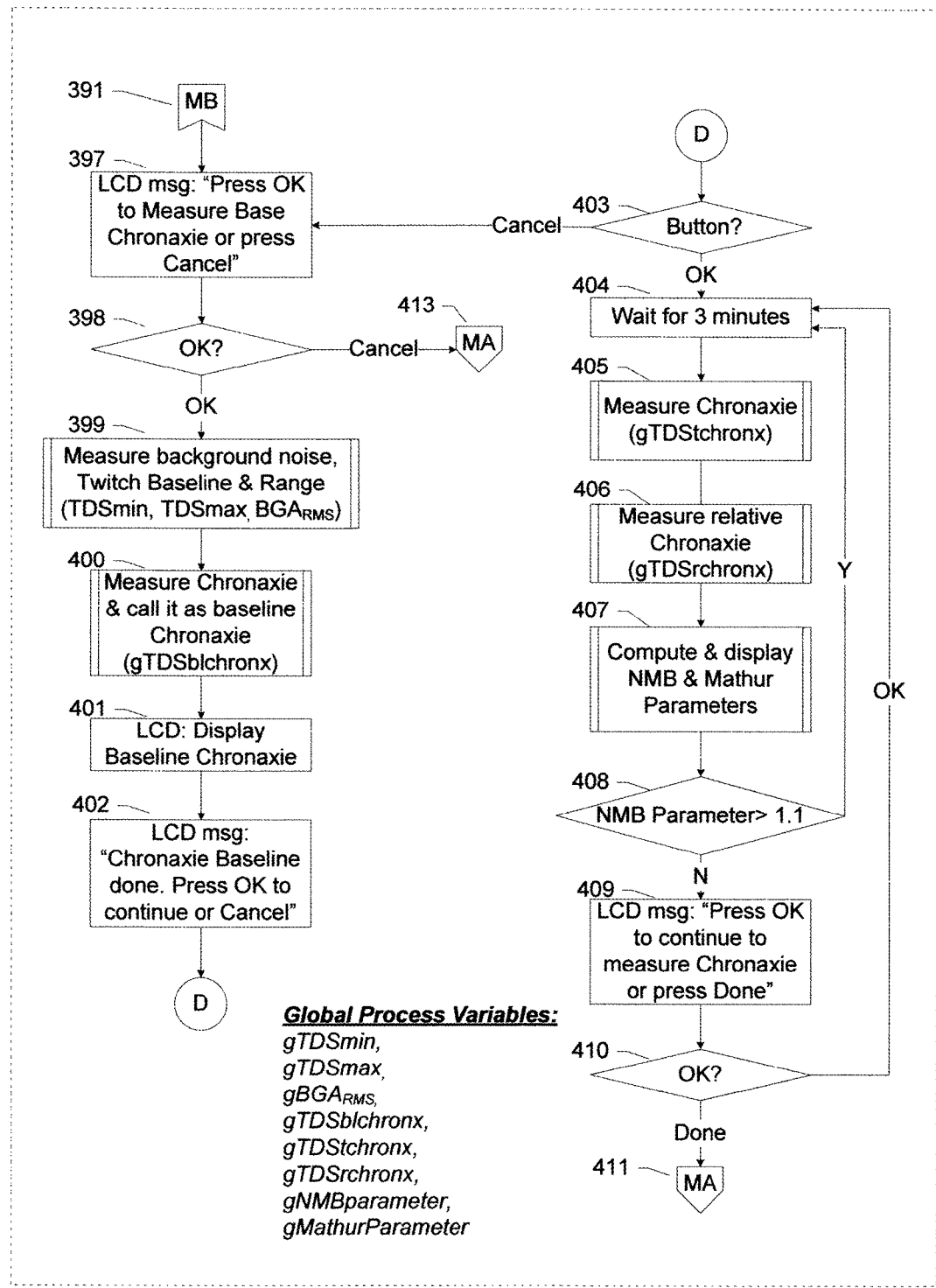

FIGS. 21A and 21B show the principal workflow "Normal Start" operating in infinite loop. The workflow instantiates the following global process variables: gTDSmin, gTDSmax, gBGARMS, gTDSblchronx, gTDStchronx, gTDSrchronx, gNMBparameter, and gMathurParameter.

The system first displays a "Start Menu" with choices to run major scenarios: (1) Start Anesthesia procedure; (2) Download data; or (3) Configure device parameters. (Step 372).

Next, a User can press buttons to choose menu option (step 373).

If the User scrolls to the Menu choice "Download data", a prompt appears on the display asking whether the User wishes to download the data (step 384). If the User chooses to download the data, the data will be downloaded on the removable non-volatile storage 916 for off-line analysis and archiving (step 385).

If the User scrolls to the Menu choice "Configure device parameters", a prompt appears on the display asking whether the User wishes to configure the device parameters (step 386). The User can choose to view and configure the device parameters (step 387). Examples of device parameters include J (the Pseudo-chronaxie multiplier), NfMultiplier (Noise floor multiplier), K1, and K2. K1 is a Constant to set a minimum signal to noise ratio that is suitable to ensure reliable twitch sensing. K2 is a Constant that ensures there is enough physical space to sense physiological movement to ensure there is no physical obstruction preventing movement. In some embodiments, 100>K1>3 and 20>K2>2.

If the User scrolls to the Menu choice "Start Anesthesia Procedure", a prompt appears on the display asking whether the User wishes to start the Anesthesia Procedure (step 374). If the User chooses to start the Anesthesia Procedure, the system 104 starts the operation as follows.

First, the display 106 displays an LCD displays message instructing the User to "Connect twitch sensor, and then press OK button, or to cancel press the Cancel button" (step 375). If the user chooses the Cancel button, the user interface goes back to the "Start menu" (step 372). If the user chooses the OK button, the device checks the connectivity and health of the Twitch sensor 002 (step 377). If connectivity fails, a suitable error message is displayed for few seconds along with error buzzer note (step 390) and the control transfers to 375. If the connectivity passes, the LCD displays message to "Connect stimulus cable to the electrode, and then press OK button, or to cancel press the Cancel button" (step 379). If the user chooses the Cancel button, the user interface goes back to the "Start menu" (step 372). If the user selects the OK button in step 380, the device checks the cable connectivity with the stimulus electrode 001 (step 381). If the cable connectivity fails, a suitable error message is displayed for few seconds along with error buzzer note (step 391) and the control transfers to 379.

With reference to steps 382/383 of FIG. 21A and step 391 of FIG. 21B, if the cable connectivity passes, the user will be prompted to press an OK button to measure and establish the baseline chronaxie before administering NMBA (steps 397/398). If the user presses the OK button, the workflow invokes sub-process "Measure background noise, twitch baseline and range" 399, and returns the arguments to update the similarly named global variables as follows:
gTDSmin=TDSmin
gTDSmax=TDSmax
gBGARMS=BGARMS Next, the workflow invokes the sub-process "Measure Chronaxie" (step 400), provides the argument gTDSmin, and assigns its return argument to gTDSblchronx. The workflow then updates the user display with the baseline chronaxie information (step 401).

Next, the LCD display displays a message "Chronaxie Baseline done. Press OK to continue to measure NMB parameter or Cancel to retry" to the user (step 402). If the user presses the Cancel button, control is transferred to 397. If the user presses the OK button, the workflow waits for 3 minutes before invoking the sub-process "Measure Chronaxie" (step 400), providing it with the argument gTDSmin, and assigning its return argument to gTDStchronx (the temporal chronaxie). Thereafter the workflow invokes the sub-process "Measure relative Chronaxie" (step 406), provides the argumentsgTDSblchronx and gTDSmin, and assigns its return argument to gTDSrchronx (the temporal relative chronaxie).

Next, the workflow invokes the sub-process "Compute and Display NMB and Mathur parameters" (step 407), providing it with the arguments gTDSblchronx, gTDStchronx and gTDSrchronx, and assigning its return argument to gNMBparameter and gMathurParameter.

If the gNMBparameter value is not close to one, the workflow gets into a loop to continuously monitor the NMB parameter and transfer control to 404. If the gNMBparameter value is close to one, the system displays a message "NMB parameter is close to one. To continue to monitor Chronaxie press OK, else press Done button". If the user presses OK, the workflow goes into a loop to monitor the NMB parameter and transfer control to 404. If the gNMB-parameter value is close to one, the system transfers control to reach the main menu (step 372).

In some embodiments, the system 100 can include additional functionalities. For example, the system 100 can be integrated with a controlled drug delivery system to recover the patient back to safe condition. In some embodiments, the system 100 can be integrated with other patient monitoring system(s) to measure other vital parameters to form an automated patient health monitoring system. The other patient monitoring system(s) can be capable of measuring, for example, ECG (Electro Cardio Gram), Heart pulse rate, Blood Pressure, or Blood oxygen.

In some embodiments, the system 100 can include sensor algorithms that determine/measure a patient's health status.

In some embodiments, the system 100 can include software that integrates patient health status and computes the corrective medication required to stabilize and recover a patient. For example, the system can be configured to automatically administer medication (e.g. intravenous drip) from a bank of medications whose dose can be electronically controlled. In some instances, the system can be configured to administer medication semi-automatically (e.g., where there is doctor in the loop to approve before medication can be administered).

In some embodiments, the system 100 can be used to automatically administer drug to reverse the NMB, based on the NMB measurements.

In some embodiments, the system 100 can be included as part of a medical aid kit to be used in an event of NBC (Nuclear Biological Chemical) weapon use.

In some embodiments, the thumb unit can include one or more of the following sensors, such as Twitch sensor (accelerometers and rate gyros), Heart pulse rate sensor, Blood pressure sensor, or Blood oxygen sensor.

In some embodiments, the system 100 can be configured to consume low energy when eliciting a neuromuscular response from a muscle, by operating at a pulse duration to utilize lesser amount of electric charge and/or implementing a modified binary search algorithm to determine optimum current $I_2$ or optimum pulse period $PC_2$.

In some embodiments, the thumb sensor in the system 100 can be used in conjunction with a traditional Peripheral Nerve Stimulator (PNS) to detect patient response to neuromuscular stimulus from the Peripheral Nerve Stimulator. The value added there accurately senses the vector amplitude (in 2 or 3 orthogonal directions) of initial stroke (before administering NMB drug) so that patient's recovery can be measured to match initial (healthy) neuromuscular response.

Accordingly, the system 100 can provide an objective/recordable evidence of the patient having recovered to his normal (healthy state) neuro-muscular state.

The system 100 can also assist in titrating relaxant drugs versus NMBRA drugs. This reduces the unwanted serious side effects of the reversal drugs (antidotes) given to the patients.

The system 100 enables the end point of paralysis to be precisely determined, which can assist the anesthesia doctor in making the decision to disconnect the patient from the breathing systems and let the patient breathe on their own. This makes the anesthesia procedure a scientific procedure, rather than a subjective procedure depending on "experience" only.

Valuable lives can be saved after anesthesia and surgery by obtaining an objective assessment of the state of paralysis of the patient using the system 100. The dosage of antidote or NMB reversal drugs can be measured and given to the patient to reverse the paralysis caused by earlier administration of the NMB drugs at the beginning of the anesthesia and surgery. Accordingly, no residual damage/pain produced or left in the patient.

Although exemplary embodiments of the present invention has been shown and described, it should be apparent to those of ordinary skill that a number of changes and modifications to the invention may be made without departing from the spirit and scope of the invention. This invention can readily be adapted to such devices by following the present teachings. All such changes, modifications, and alterations should therefore be recognized as falling within the scope of the present invention.

What is claimed is:

1. A computer-implemented method for quantitatively determining a person's neuro-muscular blockade (NMB) level in real-time using a sensor attached to the person, the method comprising:

generating an electrical stimulus that is applied to the sensor;

receiving a first input signal from the sensor, wherein the first input signal includes a measurement of a first muscular response made by the sensor, the first muscular response resulting from a first stimulus current ($I_1$) delivered to the person before administration of NMB agents to the person;

establishing, via a micro-computer that is connected to the sensor, a baseline chronaxie ($PC_1$) based on the first input signal;

delivering, via the sensor, one or more second stimulus currents ($I_{current}$) to the person for one or more time durations that are the same as or longer than the baseline chronaxie ($PC_1$), after the administration of NMB agents to the person;

receiving a second input signal from the sensor, wherein the second input signal includes a measurement made by the sensor of one or more second muscular responses resulting from the one or more second stimulus currents ($I_{current}$);

determining, via the micro-computer, a temporal chronaxie ($PC_{current}$) based on the second input signal;

calculating a chronaxie ratio of temporal chronaxie ($PC_{current}$) to baseline chronaxie ($PC_1$); and determining, via the micro-computer, the person's NMB level based on the chronaxie ratio, determining, via the micro-computer, an amount of NMB agents or an amount of NMB reversing agents to administer to the person, based on at least the person's determined NMB level; and administering, via a drug delivery system connected to the micro-computer, the determined amounts of NMB agents or NMB reversing agents to the person.

2. The method of claim 1, further comprising delivering each of the one or more second stimulus currents ($I_{current}$) for a duration of the baseline chronaxie.

3. The method of claim 2, wherein determining the person's NMB level based on the second input signal comprises:

determining the person's NMB level based on a current ratio of the particular stimulus current ($I_{current}$) to the first stimulus current ($I_1$).

4. The method of claim 3, wherein the one or more second stimulus currents ($I_{current}$) are greater than the first stimulus current ($I_1$).

5. The method of claim 1, wherein the sensor is configured to measure at least one of angular acceleration, angular velocity, angular displacement, linear acceleration, linear velocity, and linear displacement.

6. The method of claim 1, wherein the sensor is configured to be attached to different parts of the person's body including the thumb or face area near the eyes.

7. The method of claim 1, wherein the sensor is further configured to measure at least one of ECG (Electro Cardio Gram), heart pulse rate, blood pressure, and blood oxygen.

8. The method of claim 1, further comprising determining the person's new NMB level after the determined amounts of NMB agents or NMB reversing agents have been administered.

9. An apparatus for quantitatively determining a person's neuromuscular blockade (NMB) level in real-time using a sensor attached to the person, the apparatus comprising:
 a stimulus electrode, the stimulus electrode configured to deliver a stimulus current to the person for a time duration that is longer than the baseline chronaxie;
 the sensor receiving a signal including a measurement of the muscular response to the stimulus current, the sensor being coupled to the stimulus electrode; and
 a paralysis assessment system including a micro-computer configured to receive the signal and determine the person's NMB level based on the signal, wherein the paralysis assessment system is configured to:
 receive a first input signal from the sensor, wherein the first input signal includes a measurement of a first muscular response, the first muscular response resulting from a first stimulus current ($I_1$) delivered to the person before administration of NMB agents to the person;
 establish a baseline chronaxie ($PC_1$) based on the first input signal;
 deliver one or more second stimulus currents ($I_{current}$) to the person after the administration of NMB agents to the person;
 receive a second input signal from the sensor, wherein the second input signal includes a measurement of one or more second muscular responses resulting from the one or more second stimulus currents ($I_{current}$);
 determine a temporal chronaxie ($PC_{current}$) based on the second input signal; and
 determine the person's NMB level based on at least one of a chronaxie ratio of temporal chronaxie ($PC_{current}$) to baseline chronaxie ($PC_1$) and a current ratio of one of the second stimulus currents ($I_{current}$) to the first stimulus current ($I_1$);
 determine an amount of NMB agents or an amount of NMB reversing agents to administer to the person, based on at least the person's determined NMB level; and,
 a drug delivery system, connected to the paralysis assessment system, for administering the determined amounts of NMB agents or NMB reversing agents to the person.

10. The apparatus of claim 9, wherein the stimulus electrodes deliver each of the one or more second stimulus currents ($I_{current}$) for a duration of the baseline chronaxie.

11. The apparatus of claim 9, wherein the one or more second stimulus currents ($I_{current}$) are greater than the first stimulus current ($I_1$).

12. The apparatus of claim 9, wherein the sensor is configured to measure at least one of angular acceleration, angular velocity, angular displacement, linear acceleration, linear velocity, and linear displacement.

13. The apparatus of claim 9, wherein the sensor is configured to be attached to different parts of the person's body including the thumb or face area near the eyes.

14. The apparatus of claim 9, wherein the sensor is further configured to measure at least one of ECG (Electro Cardio Gram), heart pulse rate, blood pressure, and blood oxygen.

15. The apparatus of claim 9, wherein the paralysis assessment system is further configured to determine the person's new NMB level after the determined amounts of NMB agents or NMB reversing agents have been administered by the drug delivery system.

16. The apparatus of claim 9, further comprising a Peripheral Nerve Stimulator (PNS) for providing neuromuscular stimulus, wherein at least one sensor is further configured to detect a muscular response resulting from the neuromuscular stimulus.

17. A non-transitory computer-readable medium storing instructions that, when executed; causes a computer to perform a method for quantitatively determining a person's neuro-muscular blockade (NMB) level in real-time using at least one sensor attached to the person, the method comprising:
 generating an electrical stimulus that is applied to the sensor;
 receiving a first input signal from the sensor, wherein the first input signal includes a measurement of a first muscular response made by the sensor, the first muscular response resulting from a baseline stimulus current delivered to the person before administration of NMB agents to the person;
 establishing, via a micro-computer that is connected to the sensor, a baseline chronaxie ($PC_1$) based on the first input signal;
 delivering, via the sensor, one or more stimulus currents ($I_{current}$) to the person for one or more time durations that are longer than the baseline chronaxie ($PC_1$), after the administration of NMB agents to the person;
 receiving a second input signal from the sensor, wherein the second input signal includes a measurement made by the sensor of one or more muscular responses resulting from the one or more stimulus currents ($I_{current}$);
 determining, via the micro-computer, a temporal chronaxie ($PC_{current}$) based on the second input signal; and
 determining, via the micro-computer, the person's NMB level based on at least one of a chronaxie ratio of temporal chronaxie ($PC_{current}$) to baseline chronaxie ($PC_1$) and current ratio of one of the second stimulus currents ($I_{current}$) to the first stimulus current ($I_1$),
 determining, via the micro-computer, an amount of NMB agents or an amount of NMB reversing agents to administer to the person, based on at least the person's determined NMB level, and
 administering, via a drug delivery system connected to the micro-computer, the determined amounts of NMB agents or NMB reversing agents to the person.

* * * * *